United States Patent [19]
Kelly

[11] Patent Number: 6,034,211
[45] Date of Patent: Mar. 7, 2000

[54] β-SHEET NUCLEATING PEPTIDOMIMETICS

[76] Inventor: Jeffery W. Kelly, 213 Chimney Hill Cir., College Station, Tex. 77840

[21] Appl. No.: 08/664,379

[22] Filed: Jun. 14, 1996

Related U.S. Application Data

[60] Provisional application No. 60/018,925, Jun. 3, 1996.

[51] Int. Cl.[7] .................................................. C07K 5/00
[52] U.S. Cl. ..................................... 530/317; 546/101
[58] Field of Search ........................... 548/427; 546/101; 514/323–328; 530/317

[56] References Cited

PUBLICATIONS

Jarrett et al., "The Carboxy Terminus of the β Amyloid Protein Is Critical for the Seeding of Amyloid Formation: Implications for the Pathogenesis of Alzheimer's Disease", Biochemistry 32:4693–4697, 1993.

Klunk et al., "Quantitative Evaluation of Congo Red Binding to Amyloid–like Proteins with a Beta–pleated Sheet Conformation", J. Histochemistry and Cytochemistry 37:1273–1281, 1989.

Lai et al., "The Acid–Mediated Denaturation Pathway of Transthyretin Yields a Conformational Intermediate That Can Self–Assemble into Amyloid", Biochemistry, 35:6470–82 (1996).

LeVine, "Thioflavine T Interaction with Amyloid β–Sheet Structures", Amyloid: Int. J. Exp. Clin. Invest., 2:1–6 (1995).

Lomakin et al., "On the nucleation and growth of amyloid β–protein fibrils: Detection of nuclei and quantitation of rate constants", Proc. Natl. Acad. Sci. 93:1125–1129, 1996.

Smith et al., "Guidelines for Protein Design: The Energetics of βSheet Side Chain Interactions", Science 270:980–982, 1995.

Tjernberg et al., "Arrest of β–Amyloid Fibril Formation by a Pentapeptide Ligand", J. Biol. Chem., 271: 8545–8548, 1996.

Tsang et al., "Hydrophobic Cluster Formation Is Necessary for Dibenzofuran–Based Amino Acids to Function as β–Sheet Nucleators", J. Am. Chem. Soc. 116:3988–4005, 1994.

Bekele et al., J. Org. Chem. 62:2259–2262 (1997).

Diaz et al., Tetrahedron Lett. 32:5725–5728 (1991).

Choo et al., Macromolucules 29:355–366 (1996).

Diaz et al., Tetrahedron 49:3533–3545 (1993).

Diaz et al., J. Am. Chem. Soc. 115:3790–3791 (1993).

Diaz et al., J. Am. Chem. Soc. 114:8316–8318 (1992).

LeBrenz et al., Peptidomimetic Host That Binds a Peptide Guest Affording a Beta–Sheet Structure That Subsequently Self–Assembles, A Simple Receptor Mimetic, J. Am. Chem. Soc. 117:1655–1656 (1995).

Graciani, Amino Acids the Specify Structure Through Hydrophobic Clustering and Histidine–Aromatic Interactions Lead to Biologically Active Peptidomimetics, Bioorganic & Medicinal Chemistry 2:999–1006 (1994).

*Primary Examiner*—Sheela Huff
*Attorney, Agent, or Firm*—Fish & Richardson P.C.

[57] ABSTRACT

N-methylated β-sheet nucleating peptidomimetics containing diarylheterocycle β-turn mimics, and methods of making and using them.

13 Claims, No Drawings

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 7 amino acids
       (B) TYPE: amino acid
       (D) TOPOLOGY: linear (ii) MOLECULE TYPE: peptide (ix) FEATURE:
       (B) LOCATION: 2...2
       (D) OTHER INFORMATION: wherein Xaa at position 2 is Ornithine (ix) FEATURE:
       (B) LOCATION: 4...4
       (D) OTHER INFORMATION: wherein Xaa at position 4 is
           3-(2-aminoethyl)(2'-propanoyl)-biphenyl (ix) FEATURE:
       (B) LOCATION: 6...6
       (D) OTHER INFORMATION: wherein Xaa at position 6 is Ornithine (xi) SEQUENCE DESCRIPTION: SEQ ID NO:1:

Val Xaa Leu Xaa Val Xaa Leu
 1               5

(2) INFORMATION FOR SEQ ID NO:2:

```
    (i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (B) LOCATION: 2...2
        (D) OTHER INFORMATION: wherein Xaa at position 2 is Ornithine (ix) FEATURE:
        (B) LOCATION: 4...4
        (D) OTHER INFORMATION: wherein Xaa at position 4 is
            3-(2-aminoethyl)(2'-propanoyl)-biphenyl (ix) FEATURE:
        (B) LOCATION: 6...6
        (D) OTHER INFORMATION: wherein Xaa at position 6 is Ornithine (xi) SEQUENCE DESCRIPTION: SEQ ID NO:2:

Val Xaa Phe Xaa Val Xaa Leu
 1               5

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (B) LOCATION: 4...4
        (D) OTHER INFORMATION: wherein Xaa at position 4 is
            3-(2-aminoethyl)(2'-propanoyl)-biphenyl (ix) FEATURE:
        (B) LOCATION: 6...6
        (D) OTHER INFORMATION: wherein Xaa at position 6 is Ornithine (xi) SEQUENCE DESCRIPTION: SEQ ID NO:3:

Val Glu Leu Xaa Val Xaa Leu
 1               5

(2) INFORMATION FOR SEQ ID NO:4:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (B) LOCATION: 7...7
        (D) OTHER INFORMATION: wherein Xaa at position 7 is
            3-(2-aminoethyl)(2'-propanoyl)-biphenyl (xi) SEQUENCE DESCRIPTION: SEQ ID NO:4:

Lys Val Lys Val Lys Leu Xaa Val Lys Val Lys Val Lys
 1               5                  10

(2) INFORMATION FOR SEQ ID NO:5:

(i) SEQUENCE CHARACTERISTICS:
        (A) LENGTH: 13 amino acids
        (B) TYPE: amino acid
        (D) TOPOLOGY: linear (ii) MOLECULE TYPE: peptide
```

(ix) FEATURE:
                  (B) LOCATION: 7...7
                  (D) OTHER INFORMATION: wherein Xaa at position 7 is
                       (2-amino)(3'-propanoyl)-biphenyl (xi) SEQUENCE DESCRIPTION: SEQ ID NO:5:

Lys Val Lys Val Lys Leu Xaa Val Lys Val Lys Val Lys
 1               5                  10

(2) INFORMATION FOR SEQ ID NO:6:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (ix) FEATURE:
            (B) LOCATION: 7...7
            (D) OTHER INFORMATION: wherein Xaa at position 7 is
                  3-(2-aminoethyl)(2'-propanoyl)-biphenyl (xi) SEQUENCE DESCRIPTION: SEQ ID NO:6:

Val Lys Val Lys Val Lys Xaa Lys Val Lys Val Lys Val
 1               5                  10

(2) INFORMATION FOR SEQ ID NO:7:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (ix) FEATURE:
            (B) LOCATION: 3...3
            (D) OTHER INFORMATION: wherein Xaa at position 3 is
                  N-Methylisoleucine (ix) FEATURE:
            (B) LOCATION: 7...7
            (D) OTHER INFORMATION: wherein Xaa at position 7 is
                  3-(2-aminoethyl)(2'-propanoyl)-biphenyl (ix) FEATURE:
            (B) LOCATION: 11...11
            (D) OTHER INFORMATION: wherein Xaa at position 11 is
                  N-Methylisoleucine (xi) SEQUENCE DESCRIPTION: SEQ ID NO:7:

Lys Val Xaa Val Lys Leu Xaa Val Lys Val Xaa Val Lys
 1               5                  10

(2) INFORMATION FOR SEQ ID NO:8:

(i) SEQUENCE CHARACTERISTICS:
            (A) LENGTH: 14 amino acids
            (B) TYPE: amino acid
            (D) TOPOLOGY: linear (ii) MOLECULE TYPE: peptide (xi) SEQUENCE DESCRIPTION: SEQ ID NO:8:

Lys Val Lys Val Lys Val Gly Gly Val Lys Val Lys Val Lys
 1               5                  10

(2) INFORMATION FOR SEQ ID NO:9:

(i) SEQUENCE CHARACTERISTICS:

```
            (A) LENGTH: 5 amino acids
            (B) TYPE: amino acid
            (D) TOPOLOGY: linear (ii) MOLECULE TYPE: peptide (ix) FEATURE:
            (B) LOCATION: 3...3
            (D) OTHER INFORMATION: wherein Xaa at position 3 is
                4-(2-aminoethyl)(6'-propanoyl)-dibenzofuran (xi) SEQUENCE DESCRIPTION: SEQ ID NO:9:

Lys Leu Xaa Val Glu
 1               5

(2) INFORMATION FOR SEQ ID NO:10:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (ix) FEATURE:
            (B) LOCATION: 7...7
            (D) OTHER INFORMATION: wherein Xaa at position 7 is
                4-(2-aminoethyl)(6'-propanoyl)-dibenzofuran (xi) SEQUENCE DESCRIPTION: SEQ ID NO:10:

Leu Met Val Lys Leu Leu Xaa Val Val Glu Ile Phe Arg
 1               5                  10

(2) INFORMATION FOR SEQ ID NO:11:

(i) SEQUENCE CHARACTERISTICS:
            (A) LENGTH: 7 amino acids
            (B) TYPE: amino acid
            (D) TOPOLOGY: circular (ii) MOLECULE TYPE: peptide (ix) FEATURE:
            (B) LOCATION: 4...4
            (D) OTHER INFORMATION: wherein Xaa at position 4 is
                4-(2-aminoethyl)(6'-propanoyl)-dibenzofuran (xi) SEQUENCE DESCRIPTION: SEQ ID NO:11:

Lys Phe Ile Xaa Val Phe Lys
 1               5

(2) INFORMATION FOR SEQ ID NO:12:

(i) SEQUENCE CHARACTERISTICS:
            (A) LENGTH: 6 amino acids
            (B) TYPE: amino acid
            (D) TOPOLOGY: circular (ii) MOLECULE TYPE: peptide (ix) FEATURE:
            (B) LOCATION: 3...3
            (D) OTHER INFORMATION: wherein Xaa at position 3 is
                4-(2-aminoethyl)(6'-propanoyl)-dibenzofuran (ix) FEATURE:
            (B) LOCATION: 6...6
            (D) OTHER INFORMATION: wherein Xaa at position 6 is
                4-(2-aminoethyl)(6'-propanoyl)-dibenzofuran (xi) SEQUENCE DESCRIPTION: SEQ ID NO:12:

His His Xaa Val Phe Xaa
```

```
            1               5

(2) INFORMATION FOR SEQ ID NO:13:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (B) LOCATION: 7...7
        (D) OTHER INFORMATION: wherein Xaa at position 7 is
              4-(2-aminoethyl)(6'-propanoyl)-dibenzofuran (xi) SEQUENCE DESCRIPTION: SEQ ID NO:13:

Lys Ile Phe Tyr Ile Leu Xaa Val Leu Phe Tyr Ala Lys
 1               5                  10

(2) INFORMATION FOR SEQ ID NO:14:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (B) LOCATION: 7...7
        (D) OTHER INFORMATION: wherein Xaa at position 7 is
              4-(2-aminoethyl)(6'-propanoyl)-dibenzofuran (xi) SEQUENCE DESCRIPTION: SEQ ID NO:14:

Lys Phe Glu Ile Phe Val Xaa Leu Met Val Lys Val Lys
 1               5                  10

(2) INFORMATION FOR SEQ ID NO:15:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (B) LOCATION: 4...4
        (D) OTHER INFORMATION: wherein Xaa at position 4 is
              4-(2-aminoethyl)(6'-propanoyl)-dibenzofuran (ix) FEATURE:
        (B) LOCATION: 5...5
        (D) OTHER INFORMATION: wherein Xaa at position 5 is
              Norleucine (xi) SEQUENCE DESCRIPTION: SEQ ID NO:15:

Arg Ile His Xaa Xaa Val
 1               5

(2) INFORMATION FOR SEQ ID NO:16:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (B) LOCATION: 8...8
```

```
        (D) OTHER INFORMATION: wherein Xaa at position 8 is
            4-(2-aminoethyl)(6'-propanoyl)-dibenzofuran (xi) SEQUENCE DESCRIPTION: SEQ ID NO:16:

Lys Thr Phe Val Val Glu Val Xaa Tyr Ser Thr Thr Ala Val Lys Lys
 1               5                  10                  15

(2) INFORMATION FOR SEQ ID NO:17:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:17:

Lys Leu Val Phe
 1

(2) INFORMATION FOR SEQ ID NO:18:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (ix) FEATURE:
          (B) LOCATION: 3...3
          (D) OTHER INFORMATION: wherein Xaa at position 3 is Val, Phe,
              Ala or a non-natural hydrophobic alpha-amino acid residue (ix) FEATURE:
          (B) LOCATION: 4...4
          (D) OTHER INFORMATION: wherein Xaa at position 3 is Val, Phe,
              Ala or a non-natural hydrophobic alpha-amino acid residue (xi) SEQUENCE DESCRIPTION: SEQ ID NO:18:

Lys Leu Xaa Xaa Phe
 1               5

(2) INFORMATION FOR SEQ ID NO:19:

(i) SEQUENCE CHARACTERISTICS:
          (A) LENGTH: 6 amino acids
          (B) TYPE: amino acid
          (D) TOPOLOGY: linear (ii) MOLECULE TYPE: peptide (ix) FEATURE:
          (B) LOCATION: 1...1
          (D) OTHER INFORMATION: wherein Xaa at position 1 is Ornithine (xi) SEQUENCE DESCRIPTION: SEQ ID NO:19:

Xaa Lys Leu Val Phe Phe
 1               5
```

β-SHEET NUCLEATING PEPTIDOMIMETICS

RELATED APPLICATIONS

This utility application claims priority from provisional application Ser. No. 60/018,925, filed on Jun. 3, 1996.

STATEMENT AS TO FEDERALLY SPONSORED RESEARCH

This invention was made with support from the National Institutes of Health (Grant R01 GM51105). Accordingly, the U.S. government may have certain rights in this invention.

BACKGROUND OF THE INVENTION

Reverse-turns are structures which reverse the direction of a polypeptide chain. When they connect antiparallel β-strands, the reverse turns are also known as β-turns, β-bends, and hairpin turns. Reverse-turns can be described as tetrapeptide sequences. However, the most critical parameters are the the torsion angles of the second and third residues. The first and fourth residues may or may not form hydrogen bonds. As a result of geometric requirements, Asn, Ser, Asp, and particularly Gly or Pro are often present.

SUMMARY OF THE INVENTION

This invention is related to unnatural amino acids which nucleate β-structures.

One aspect of the invention is a method of making an asymmetrical, substituted dibenzoheterocycle, including (a) deprotonating a 4-substituted dibenzoheterocycle having the formula ii:

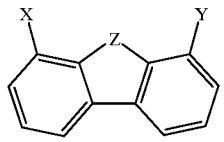

(ii)

wherein X is a substituent inert to treatment with strong base, Y is H, and Z is O, S, SO$_2$, or NR$_a$, R$_a$ being C$_{1-6}$ alkyl in an aprotic solvent with a strong base; and (b) adding an excess of 2 molar equivalents of an electrophile, thereby forming an asymmetrical 4,6-bis-substituted dibenzoheterocycle.

Another aspect of the invention is an asymmetrical, substituted dibenzoheterocycle having the formula I:

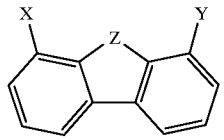

(I)

X is F, Cl, Br, I, 3-propenoic acid, C$_{1-10}$ alkylpropenylate, or C$_{6-10}$ arylpropenylate; Y is tri(C$_{1-10}$ alkyl)silyl, tri(C$_{2-10}$ alkenyl)silyl, di(C$_{1-10}$ alkyl) (C$_{2-10}$ alkenyl)silyl, di(C$_{2-10}$ alkenyl) (C$_{1-10}$ alkyl)silyl, C$_{1-6}$ alkenylthio, C$_{1-6}$ alkylthio, C$_{1-6}$ alkyl-seleno, C$_{1-6}$ alkenylseleno, C$_{1-10}$ alkylpropenylate, or C$_{6-10}$ arylpropenylate, wherein X and Y are not the same. Z is O, S, NR$_i$, or SO$_2$, R$_i$ being C$_{1-6}$ alkyl.

A third aspect of the invention features a β-sheet nucleating peptidomimetic which includes a diarylheterocycle, a recognition strand, and a blocking strand. The peptidomimetic ("mimetic") can be acyclic or cyclic. Diarylheterocycle has the formula II:

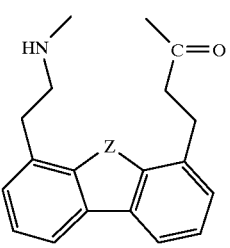

(II)

or the formula III:

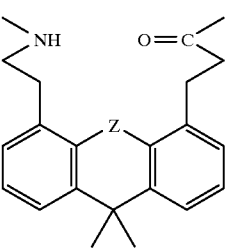

(III)

Z is O, S, or NR$_a$, R$_a$ being C$_{1-6}$ alkyl. The recognition strand has between 3 and 21 amino acid residues, and includes a recognition sequence of a target protein which requires self-assembly for function, and a flanking residue (r$^1$). The flanking residue r$^1$ is selected from histidine and hydrophobic amino acids, wherein r$^1$ is between the recognition sequence and the diarylheterocycle, and is linked to the diarylheterocycle by an amide bond. The recognition strand is linked via the flanking residue r$^1$ to either the C- or N-terminus of the diarylheterocycle. The recognition strand also includes at least one N-methylated residue adjacent to an intramolecularly hydrogen bonded residue.

The blocking strand, generally between 3 and 21 amino acid residues includes a flanking residue (b$^1$) selected from histidine and hydrophobic amino acids. The flanking residue b$^1$ is between the blocking sequence and the diarylheterocycle, and is linked to the diarylheterocycle by an amide bond. The blocking strand includes at least one residue selected from valine, leucine, and isoleucine, and at least one N-methylated residue adjacent to an intramolecularly hydrogen-bonded residue.

Selection of interstrand interaction-promoting pairs of residues (one member of each pair being in the recognition strand and the other being in the blocking strand) provides conformational control. Such interstrand interaction includes intramolecular hydrogen bonding and hydrophobic clustering. β-sheet nucleating mimetics generally have a high degree of interstrand interaction. However, cyclic mimetics may contain bubble- or loop-like portions of the sequence which do not interact.

The invention also features various methods of using the above-described β-turn mimics, and β-sheet nucleating peptidomimetics. One example is a method of treating a cross-β amyloid fibril-mediated disease, including administering to a patient in need of such treatment an effective amount of a peptidomimetic of the invention and a pharmaceutically acceptable carrier, thereby treating a cross-β amyloid fibril-mediated disease.

DETAILED DESCRIPTION OF THE INVENTION

A. Terms

Some terms are defined below and by the remainder of the disclosure. For illustrative purposes, dibenzofuran and its derivatives are referenced below in the synthetic discussion, although derivatives of dibenzothiofuran and 9,9-dimethylxanthene, for example, are within the invention.

A strong base is capable of removing both the 4- and 6-position protons of dibenzofuran. A strong base will therefore provide a high yield (e.g., at least 75%, and preferably at least 85%) of 4-trimethylsilyl-6-anion dibenzofuran species when 4-trimethylsilyl-dibenzofuran is treated with more than 1 equivalent of a strong base at 0° C. in THF. Strong bases include organosodium reagents, organopotassium reagents, and preferably, alkyl lithium reagents in the presence of 1 base-equivalent of N,N,N',N'-tetramethylethylenediamine.

A moderate base is capable of removing one of the 4- and 6-position protons of dibenzofuran, but not capable of removing both protons simultaneously in high yield. Preferably, 1.2 equivalents of a moderate base will yield no more than 5% of the 4,6-dianion of dibenzofuran in THF at 0° C. Adding more than one equivalent of a moderate base to dibenzofuran provides a high yield of the 4-position monoanion. Moderate bases include n-butyllithium, sec-butyllithium, and t-butyllithium.

The preferred solvents in the synthesis of asymmetrical dibenzofuran derivatives and related compounds such as 9,9-dimethylxanthene and dibenzothiofuran analogs are aprotic solvents. An aprotic solvent will not be deprotonated in the presence of a strong base or a moderate base, as defined above. An appropriate solvent must solubilize dibenzofuran derivatives and anions, base reagents, and other reagents such as electrophiles. Aprotic solvents include tetrahydrofuran, diethyl ether, glyme, and other ether-type solvents, or solvent systems containing combinations of solvents.

As used herein, electrophiles form a bond to the $sp^2$ hybridized 4- or 6-position carbon atoms, using an electron pair from a metallated dibenzofuran or analogous compound. Where there is a first and second electrophile, the first electrophile after bonding to the 4- or 6-position must be inert to a strong base. Furthermore, the first electrophile must be capable of conversion to a reactive functional group. Suitable electrophiles include trialkylsilyl halides, triarylsilyl halides, chlorine, bromine, iodine, fluorinating agents, trialkylborates (e.g., pinacol ester of methyl borate, and trimethylborate), halides ($I_2$ and $Br_2$), and halogenating agents such as carbontetrachloride, carbontetrabromide, diiodomethane, carbon dioxide, halonium ions, alkyltriflates, oxonium ions, aldehydes, ketones, imines, epoxides, aziridines, alkyl halides, alkenyl halides, acyl halides, sulfonium ions, diazonium salts, electron deficient metals, sulfur dioxide, nitriles, dimethylsulfate, dialkylsulfides, dialkyl-selenides, diarylsulfides, diarylselenides, alkylformates and aryl formates.

Preferred electrophiles that can be converted into reactive functional groups include $R_3SiX$, RSeSeR', and RSSR', wherein each R is independently selected from alkyl, alkenyl, and aryl, and X is halogen (preferably chloride), R' is phenyl, t-butyl, and 2-pyridinyl. In some embodiments, R is alkyl or alkenyl; R is $C_{1-6}$ alkyl or $C_{2-6}$ alkenyl; R is $C_{1-3}$ alkyl or $C_{2-3}$ alkenyl. In some embodiments, electrophiles such as alkyl halides and alkenyl halides; alkyl halides are less preferred due to increased susceptibility to deprotonation Where asymmetrical, bis-substituted derivatives are desired, either one electrophile is used (the other position being H), or two different electrophiles are used in sequence. Obviously, symmetrical bis-substituted derivatives are provided when the first and second electrophiles are the same.

Alkyl groups include straight chain alkyls such as methyl, ethyl, propyl, butyl, and pentyl; branched alkyls such as isopropyl, isobutyl, t-butyl, sec-pentyl, and 2-methyl-4-ethylheptyl; and cycloalkyls, such as cyclopentyl, cyclohexyl, and 2,4-dimethylcyclohexyl. $C_{1-10}$ alkyls, such as $C_{1-6}$ alkyls or $C_{1-3}$ alkyls. In some embodiments, trialkyl compounds have fewer than 15 carbon atoms, e.g., fewer than 10 carbon atoms, such as trimethylsilyl chloride, t-butyldimethylsilyl chloride, and isopropyldimethylsilyl chloride.

Alkenyl groups are $C_{2-10}$, e.g., $C_{2-8}$ or $C_{2-6}$. Like alkyl groups, they include straight chain, branched, and cyclic moieties. A given double bond may be cis, trans, entgegen, or zusammen. When two or more double bonds are present, they may be conjugated or unconjugated. Alkynyl groups are $C_{2-10}$, $C_{2-8}$ or $C_{2-6}$. An alkynyl group may also include one or more double bonds and a triple bond.

B. Asymmetrical, 4,6-bis-substituted dibenzoheterocycles

One aspect of the invention features asymmetrical 4,6-bis-substituted dibenzoheterocycles including 4,6-bis-substituted dibenzofurans (formula IV) and analogous thiofurans (formula V), and the sulfonyl and sulfoxide analogs, although sulfoxide analogs are less preferred.

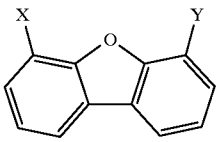

IV

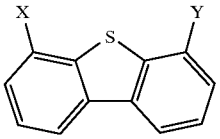

V

In these formulas, X is H, iodo, chloro, bromo, or fluoro, and preferably a halogen. Y is H, or a moiety corresponding to an electrophile, as defined in the Terms section above. Z is O, S, SO, $SO_2$, NR such as N-methyl or N-ethyl, or SiRR', wherein each of R and R' is independently selected from $C_{1-6}$ alkyl.

In certain compounds of formula I as described in the Summary section, one or more of the following apply: X is Br or I; X is iodo, bromo, 3-propenoic acid, $C_{1-10}$ alkylpropenylate, or $C_{6-10}$ arylpropenylate; and Y is tri($C_{1-10}$ alkyl)silyl, $C_{1-10}$ alkylpropenylate, or $C_{6-10}$ arylpropenylate; Z is O; X is F, Cl, Br, or I, and Y is trimethylsilyl.

The disclosed diarylheterocycles are useful as synthetic reverse-turns, namely, isosteres of the backbone of the second and third residues in naturally occurring reverse-turns. The isostere changes or reverses the direction of the polypeptide or peptidomimetic by providing the torsional angles and approximate bond distances of the two central residues in natural reverse-turns. The isostere is therefore a class of dipeptide mimetic.

C. Synthetic Methods: Asymmetrical, 4,6-bis-substituted Diarylheterocycles.

A second aspect of the invention features a method of making an asymmetrical, bis-substituted diarylheterocycle. A sequential deprotonation-electrophile addition reaction is performed once or twice, depending on the starting material, with high selectivity to provide numerous asymmetrical, 4,6-disubstituted derivatives, such as 4-iodo-6-trimethylsilyl dibenzofuran. The synthesis of representative asymmetrical bis-substituted dibenzofurans, disclosed herein, is easily adapted by a person of ordinary skill to provide corresponding asymmetrical intermediates and derivatives of other diarylheterocycles. In addition to dibenzofurans, dibenzoheterocycles include dibenzothiofuran (dibenzothiophene); dibenzo-N-$C_{1-6}$alkylpyrrole (N-alkylcarbazole) such as dibenzo-N-methylpyrrole; 9,9-di($C_{1-3}$ alkyl)xanthene derivatives such as 9,9-dimethylxanthene; dibenzo (dialkylsilacyclopentadiene); and diarylheterocycles where the oxygen of diarylfuran is replaced with SO or $SO_2$.

4-iodo-6-trimethylsilyldibenzofuran is easily functionalized (e.g., alkylated via a Heck reaction) via the aryliodide functional group. The remaining TMS is converted into a second iodo by ICl treatment to yield an aryliodide. This aryliodide undergoes any of literally hundreds of reactions including transition metal catalyzed reactions such as the Heck reaction; metallation reactions to form Grignard, cuprate lithium, or sodium adducts; nucleophilic aromatic substitution reactions employing copper catalysis such as cyano- or diethylmalonate-displacement of the iodide; and radical reactions where the radical is derived from the $sp^2$ carbon of the Ar—I bond.

1. Synthesis of 4-(2'-aminoethyl)-6-dibenzofuranpropionic acid

This aspect of the invention features an efficient synthesis of both the Boc- and FMOC-derivatives of 4-(2-aminoethyl)-6-dibenzofuran propionic acid from commercially available dibenzofuran. Dibenzofuran was made asymmetrical by sequential metallation-silation metallation-iodination reactions in an isolated yield of 75%. The first monoanion was quenched with trimethylsilyl chloride and the resulting TMS derivative 4 was deprotonated again and quenched with iodine to yield 5. This approach desymmetrizes dibenzofuran at an early stage of the synthesis of 1 differentiating the 4 and 6 positions (see, Synthetic Scheme 1, details in Example 1). Monometallation of dibenzofuran was readily accomplished by the addition of 1.2 equivalents of n-butyllithium to a THF solution of dibenzofuran at 0° C., which was then warmed to room temperature and stirred for five hours, cooled again to 0° C. and the anion was quenched with trimethylsilyl chloride at 0° C. The reaction was allowed to warm to room temperature and was then heated at reflux for 2 h, affording 4-trimethylsilyldibenzofuran (4) in a crude yield of 99%. Metallation of 4 using 1.6 equivalents each of n-butyllithium and N,N,N',N'-tetramethylethylenediamine (TMEDA) afforded the second anion which was added to an $Et_2O$ solution of $I_2$ at −78° C. to afford 4-iodo-6- trimethylsilyldibenzofuran (5) in a 75% yield after purification for both steps. This is a considerable improvement over the differentiation obtained at the 4 and 6 positions in the esterification of diacid (2) which resulted in a 25:50:25 statistical distribution of products.

Reaction of 5 with ethylacrylate in the presence of palladium acetate, tri-ortho-tolylphosphine, and triethylamine in acetonitrile provided ethyl-6-trimethylsilyl-4-dibenzofuranacrylate (6) in 93% yield after purification by flash chromatography. Iododesilylation of 6 with ICl in carbontetrachloride in the presence of potassium carbonate provided ethyl-6-iodo-4-dibenzofuranacrylate (7) in 95% isolated yield. A second Heck reaction using acrylic acid afforded the unsaturated monoacid monoester 8 in 74% yield after purification by flash chromatography. Hydrogenation of 8 was accomplished in 1:1 ethanol:acetic acid at 13 psi $H_2$ using $PtO_2$ as a catalyst to provide ethyl-6-propionic acid-4-dibenzofuranpropionate (3) in 94% isolated yield. The unsymmetrical monoacid monoester 3 was thus obtained from dibenzofuran in six steps with an overall yield of 46%. In addition to the improved yield over previous methods, the purification process on a large scale even when using flash chromatography was easier due to the different polarities of starting material and product.

SCHEME I

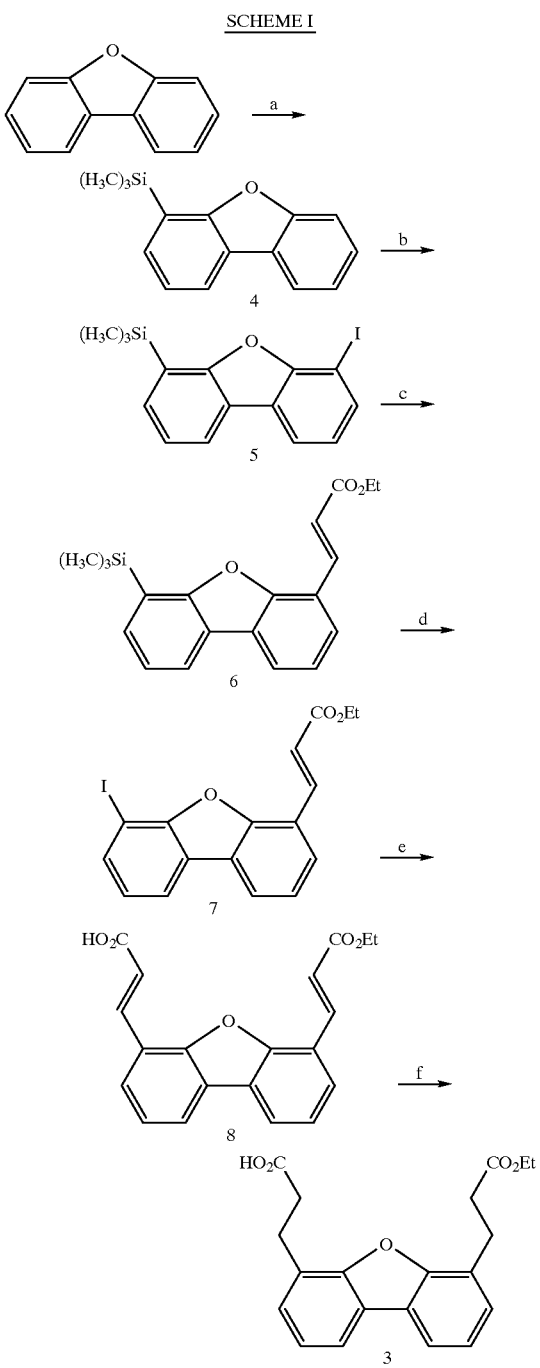

-continued

Outline of the synthesis of ethyl-6-propionic acid-4-dibenzofuran-propionate (3). Reaction conditions: (a) (i) 1.2 equiv n-BuLi in THF initially at 0° C. and then at room temperature, 5 h, (ii) 2.0 equiv TMSCl in THF at 0° C., room temperature 20 min, reflux 2 h, room temperature 12 h, 99%; (b) (i) 1.6 equiv n-BuLi, 1.6 equiv TMEDA, initially at 0° C. and then at room temperature, 5.5 h, (ii) 2.3 equiv $I_2$ in $Et_2O$, initially at -78° C. and then at room temperature, 12 h, 75%; (c) 3.0 equiv ethyl acrylate, 3.0 equiv $Et_3N$, 2.1 mol% $Pd(OAc)_2$, 5.1 mol% $P(o\text{-tol})_3$, $CH_3CN$, heated to 85° C. for 3 h, 93%; (d) 2.8 equiv ICl, 3.0 equiv $K_2CO_3$, $CCl_4$, initially at 0° C. and then at room temperature, 95%; (e) 3.0 equiv acrylic acid, 3.5 equiv $Et_3N$, 2.2 mol% $Pd(OAc)_2$, 5.0 mol% $P(o\text{-tol})_3$, $CH_3CN$, heated to 85° C. for 4 h, 74%; (f) 13 psi $H_2$, 5 mol% $PtO_2$, 1:1 HOAc:EtOH, 6.5 h, 94%.

The remainder of the synthesis of 4-(2'-aminoethyl)-6-dibenzofuranpropionic acid (1) was then accomplished by known methods to afford the Boc-N-terminally protected amino acid, or adapted to produce the FMOC-N-terminally protected derivative. One disclosed route also provides increased flexibility in the synthesis of the FMOC-N-terminally protected derivative by carrying out a Curtius rearrangement on 3. However, overall yield and ease of product isolation were improved by proceeding from the Boc derivative. TFA mediated removal of the Boc group in 9 and subsequent carbamylation with 9-fluorenylmethyloxycarbonyl-N-hydroxy succinimide (Fmoc-OSu) afforded 10 in 78% yield. Hydrolysis of the ethyl ester was achieved with 5% HCl in acetic acid to yield 11 in an isolated overall yield of 30% from dibenzofuran. The different polarities of the starting material and the product in this synthesis allows improved purification, including on a large scale or by flash chromatography, in contrast to the previously known methods. The FMOC derivative allows incorporation of the 4-(2'-aminoethyl)-6-dibenzofuran propionic acid into peptides prepared by either solid-phase strategies, namely, Fmoc and t-Boc.

An NMR analysis of heptapeptides incorporating 1 revealed the presence of a hydrogen bonded hydrophobic cluster involving an aromatic ring of 1 and side chains of the flanking hydrophobic α-amino acids residues. The flanking α-amino acid residues in these peptides exhibited significantly slower amide proton/deuterium exchange rates, indicating intramolecular hydrogen bonding between the strands in aqueous solution. These heptapeptides have a partial β-sheet structure in the sequence flanking 1 with fraying at the ends of the strands, as shown by rapid NH/$N^2$H exchange. In appropriate tridecapeptides, the hydrogen bonded hydrophobic cluster nucleates the formation of a β-hairpin structure which subsequently self-associates into a cross-β fibril. Strategically replacing two of the exterior amide protons in the tridecapeptide with methyl groups unlinked the intramolecular folding and self-association equilibria. The tertiary amide groups cannot act as hydrogen bond donors, and they sterically block the intermolecular β-sheet interactions between exterior β-strands, preventing self-assembly. The N-methylated tridecapeptide incorporating 1 was characterized by analytical equilibrium ultracentrifugation, far-UV CD, FT-IR, and a variety of NMR experiments such as COSY and NOESY which supported a β-hairpin-like structure. These peptides exhibited an increase in β-sheet structure with increasing temperature which may prove to be general for β-sheets stabilized by hydrophobic interactions.

2. Synthesis of 3'-(2-aminoethyl)-2-biphenylpropionic acid and 2-amino-3'biphenylcarboxylic acid The preparation of the 2,3'-substituted biphenyl-based amino acids 1A and 2A is known. Peptides A–G (Table I) were synthesized on benzhydrylamine resin employing standard t-Boc synthesis procedures (with BOP activation) to incorporate the α-amino acids and the t-Boc derivative of 1A into the growing peptide chain. Due to the poor reactivity of the aniline functionality of 2A, residue 2A was incorporated into peptides as a dipeptide (t-Boc-Leu-2-$CO_2$H) prepared in solution and coupled to the resin bound peptide by BOP activation. The peptides were deprotected and cleaved from the resin using high-HF and purified by reversed phase $C_{18}$HPLC. The primary structures of peptides A–G were confirmed by nominal resolution matrix-assisted laser desorption mass spectrometry.

On the basis of the NMR and CD data, it appeared that peptides incorporating the subsequence-hydrophobic α-amino acid-1A-hydrophobic α-amino acid adopted a hydrogen-bonded hydrophobic cluster conformation which can nucleate antiparallel β-sheet structure provided that the remaining α-amino acid sequence is appropriate to support a β-sheet structure. Conversely, peptides incorporating residue 2A are incapable of forming an intramolecular β-sheet structure presumably due to the inability of residue 2a to form a hydrogen-bonded hydrophobic cluster (see Example 2).

3. Methods

Embodiments of the method of making an asymmetric diarylheterocycle as described in the Summary section include the following, or combinations of the following: the strong base is n-butyllithium and tetramethylethylenediamine; the electrophile is selected from trialkylsilyl halides, triarylsilyl halides, trialkylborates, chlorine, bromine, iodine, carbontetrachloride, carbontetrabromide, diiodomethane, carbon dioxide, halonium ions, alkyltriflates, oxonium ions, aldehydes, ketones, imines, epoxides, aziridines, alkyl halides, alkenyl halides, acyl halides, sulfonium ions, diazonium salts, electron deficient metals, sulfur dioxide, nitriles, dimethylsulfate, dialkylsulfides, dialkylselenides diarylsulfides, diarylselenides, alkylformates, and arylformates, wherein each alkyl moiety is independently selected from $C_{1-10}$ alkyl, and each aryl moiety is independently selected from $C_{6-10}$ aryl; the second electrophile is chlorine, bromine, or iodine; the second electrophile is bromine or iodine; X is selected from trialkylsilyl, triarylsilyl, dialkylborates, electron deficient metals, alkylthio, alkylseleno, arylthio arylseleno, wherein each alkyl moiety is independently selected from $C_{1-10}$ alkyl, and each aryl moiety is independently selected from $C_{6-10}$ aryl; X is selected from $R_3Si$—, RSe—, and RS—, each R being independently selected from $C_{1-6}$ alkyl and $C_{2-6}$ alkenyl.

Additional embodiments include the method described in the Summary section, wherein in the adding step, the electrophile is a second electrophile, further including before the step of deprotonating with a strong base, the further step of (i) deprotonating a dibenzoheterocycle of the formula i:

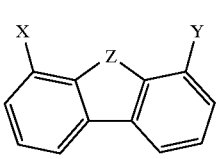

wherein each of X and Y is H, and Z is O, S, $SO_2$, or $NR_a$, $R_a$ being $C_{1-6}$ alkyl, in an aprotic solvent with a slight molar excess of a moderate base; and (ii) adding a molar excess of a first electrophile, thereby forming a monosubstituted dibenzoheterocycle, wherein the substituent corresponding to said electrophile is inert to subsequent treatment with strong base. Further embodiments include: the moderate base is n-butyllithium, sec-butyllithium, or t-butyllithium; the first electrophile is selected from trialkylsilyl halides, triarylsilyl halides, trialkylborates, carbon dioxide, diazonium salts, electron deficient metals, sulfur dioxide, dialkylsulfides, dialkylselenides, diarylsulfides, and diarylselenides, wherein each alkyl moiety is independently selected from $C_{1-10}$ alkyl, and each aryl moiety is independently selected from $C_{6-10}$ aryl; the first electrophile is selected from $R_3SiX'$, RSeSeR', and RSSR', each R being independently selected from $C_{1-6}$ alkyl and $C_{2-6}$ alkenyl, X' being fluoro, chloro, bromo, or iodo, and R' being phenyl, t-butyl, or 2-pyridinyl; the electrophile is trimethylsilylchloride; Z is O; and Z is S.

According to the invention, when a target protein is exposed to a mimetic of the invention in an aqueous solution, the recognition sequence of the mimetic binds to the target protein. The β-turn mimic and any residue pairs promoting interstrand interaction present the recognition sequence in a highly-favorable conformation for binding to the target protein. The N-methylated residue(s) on the recognition strand effectively inhibit oligomerization of the mimetic with itself, since the blocking effects of at least two N-methyl groups (at least one from the recognition strand of each mimetic) must be overcome. At the same time, the N-methyl group on the recognition strand registers the binding between the recognition sequence and the target protein, since the N-methylated residue cannot participate in hydrogen bonding. The mimetic-bound target protein is therefore unable to self-assemble into a dimer or oligomer.

TABLE 1

| Peptide | | | | R1 | R2 | R3 | R4 | R5 | R6 | R7 | | | |
|---|---|---|---|---|---|---|---|---|---|---|---|---|---|
| A | | | | Val | Orn | Leu | 1A | Val | Orn | Leu SEQ ID NO:1 | | | |
| B | | | | Val | Orn | Phe | 1A | Val | Orn | Leu SEQ ID NO:2 | | | |
| C | | | | Val | Glu | Leu | 1A | Val | Orn | Leu SEQ ID NO:3 | | | |

| Peptide | R1 | R2 | R3 | R4 | R5 | R6 | R7 | R8 | R9 | R10 | R11 | R12 | R13 |
|---|---|---|---|---|---|---|---|---|---|---|---|---|---|
| D | Lys | Val | Lys | Val | Lys | Leu | 1A | Val | Lys | Val | Lys | Val | Lys SEQ ID NO:4 |
| E | Lys | Val | Lys | Val | Lys | Leu | 2A | Val | Lys | Val | Lys | Val | Lys SEQ ID NO:5 |
| F | Val | Lys | Val | Lys | Val | Lys | 1A | Lys | Val | Lys | Val | Lys | Val SEQ ID NO:6 |
| G | Lys | Val | N—Me—Leu | Val | Lys | Leu | 1A | Val | Lys | Val | N—Me—Leu | Val | Lys SEQ ID NO:7 |
| H | Lys | Val | Lys | Val | Lys | Val | GG | Val | Lys | Val | Lys | Val | Lys SEQ ID NO:8 |

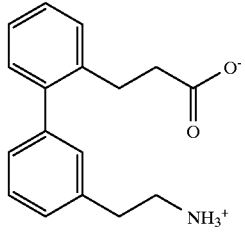

1A

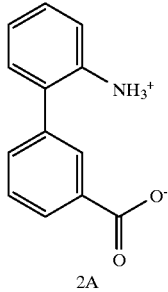

2A

D. β-structure Nucleation

A third aspect of the invention features β-sheet nucleating peptidomimetics ("mimetics"). The invention features a combination of structures to inhibit oligomerization of mimetics in solution, to provide conformational control, and to target a mimetic to a protein rich in β-sheet structure. The structural design includes N-methylated residues, a β-turn mimic, selected flanking amino acids, a preference for certain amino acid pairings for interstrand interaction, and a recognition sequence to provide specificity for the target protein.

1. General Structure

A mimetic can be divided into three main sections: (i) a β-turn mimic linked between (ii) a recognition strand and (iii) a blocking strand. In general, there is at least one N-methylated residue in each of the recognition and blocking strands to prevent oligomerization of an aqueous solution of the mimetic, particularly under physiological temperature and pH. Either the recognition strand or the blocking strand can be linked to the C-terminus of the β-turn.

For therapeutics, the total number of α-amino residues is less than 30, e.g., less than 20, less than 15, and preferably less than 12, or less than 8. The β-turn is not counted among the α-amino acid residues. Longer strands are useful for very large protein-protein interfaces. Some embodiments include cyclic structures having 4, 5, 6, 7, 8, 9 or 10 residues and linear structures having 3, 4, 5, 6, 7, 8 or 9 residues on each strand, independently. For mimetics soluble under physiological conditions, the mimetic preferably has a formal charge of between 2.0 and 4.0, e.g., between 3.0 and 4.0, at physiological pH and temperatures. Intramolecular peptide cleavage from oxime resin produces cyclized peptides.

The aromatic component of the β-turn mimic is selected from a dibenzofuran, dibenzothiofuran, or dibenzo-N-methylpyrrole derivative or analogous compound disclosed herein or known by those in the art, such as 9,9-dimethylxanthine. The β-turn mimic also includes extending $C_2$ linker moieties such as aminoethyl and propanoyl, with terminal reactive groups (amino and carbonyl, respectively) which form amide bonds with flanking residues described below.

In an acyclic mimetic, the residues of each strand can be numbered away from the β-turn, toward the free end of the blocking or recognition strand, as 1, 2, 3, etc. For example, the residues can be designated $b^1$, $b^2$, $b^3$ . . . on the blocking strand and $r^1$, $r^2$, and $r^3$ . . . on the recognition strand. A flanking residue is the first residue ($b^1$ or $r^1$) of either strand linked to the β-turn mimic. Each of the two flanking residues is independently selected from a hydrophobic α-amino acid, or histidine. Hydrophobic amino acids include Ala, Val, Leu, Ile, Phe, Trp, Tyr, and Met. The flanking residues participate in a hydrophobic interaction, or a pi-cation interaction when the flanking residue is His or Arg, with the β-turn mimic.

In addition to the flanking residue $r^1$, a recognition strand includes at least one recognition sequence. A recognition sequence is derived from a selected protein, such as a naturally-occurring enzyme or cell surface receptor, in which inhibition of self-assembly is desired. Recognition sequences can be derived from any protein whose function requires intermolecular β-sheet interaction, such as formation of a dimer, oligomer, or an exterior strand whose interaction with the mimetic would disrupt a quaternary interface other than a β-sheet. Examples of selected proteins include amyloidogenic proteins (see Table I), HIV protease (a β-sheet dimer), and viral coat proteins (e.g., influenza viral coat protein, and AIDS viral coat protein), and immunoglobulin deposition disease variants, Prp(c) from any of transmissible spongiform encephalopathies. Recognition sequences can also be derived from non-naturally occurring peptide sequences which require intermolecular β-sheet interaction for function, or where which the monomeric form is desired.

The recognition sequence is said to be derived from a selected protein because the recognition sequence may or may not be identical to the selected protein. A derived sequence can include: a partial sequence, rather than the entire protein; a plurality of partial sequences that are non-consecutive in the selected protein; one or more N-methylated residues; or a combination thereof. In some cases, a recognition sequence is between 3 and 20 residues, and preferably between 3 and 12, or 3 and 8 residues in length. For pharmaceutical utility, shorter recognition sequences are generally preferred.

Although proteolytic fragments of amyloid β-peptide have between 39 and 42 residues, the predominant form of amyloid β-peptide has 40 residues ($Aβ^{1-40}$). Each of partial sequences $Aβ^{1-28}$, $Aβ^{25-35}$, and $Aβ^{14-20}$ is known to self-associate, aggregate (e.g., form fibrils), or both. Thus each of these sequences must contain at least one recognition sequences. Amyloid β-peptide recognition sequences vary in length, and can be a short as 3, 4, 5, or 6 residues long. Recognition sequences are known to be among the ten-mers $Aβ^{9-18}$, $Aβ^{10-19}$, $Aβ^{11-20}$, $Aβ^{12-21}$, and $Aβ^{13-22}$ (e.g., Tjernberg, L. O. et al., *J. Biol. Chem.* 271:8545–8548 1996, especially FIGS. 2–4). Sequences derived from $Aβ^{11-20}$, such as KLVF SEQ ID NO:17, KLXXF SEQ ID NO:18, and OKLVFF SEQ ID NO:19, are particularly effective recognition sequences, where X is V, F, A, or a non-natural hydrophobic α-amino acid residue.

A derived sequence can also include substitution with, or insertion of, one or more residues selected to promote interstrand interaction, to adjust the overall formal charge or solubility, or to provide other structural control. One or more selected residues may be located between $r^1$ and the recognition sequence, between the recognition sequence and the terminus of the recognition strand, between two recognition sequences, or a combination thereof. Moreover, an amino acid that is critical for recognition is preferably not positioned as an N- or C-terminal residue in an acyclic mimetic.

For example, if a recognition sequence is 3 residues long, the recognition strand could contain a flanking residue ($r^1$), the recognition sequence ($r^2$–$r^4$) and one or more terminal selected residues ($r^5$, $r^5$–$r^6$, or $r^5$–$r^7$, etc.). Alternatively, the recognition strand could include the flanking residue, one or more inserted selected residues ($r^2$, $r^2$–$r^3$, or $r^2$–$r^4$, etc.), the recognition sequence (respectively, $r^3$–$r^5$, $r^4$–$r^6$, or $r^5$–$r^7$, etc.), and one terminal selected residue (respectively, $r^6$, $r^7$, or $r^8$, etc.).

In addition, a recognition strand can include a plurality of recognition sequences, optionally separated by selected residues. Each sequence in a plurality may be the same as or different from the other sequences, and may be derived from the same or different proteins. A recognition sequence which naturally presents more formal charges can more easily accommodate a longer recognition sequence. Solubility of a relatively hydrophobic recognition sequence in an aqueous (e.g., biological) fluid may be increased by adding hydrophilic residues to the recognition strand or the blocking strand, or both.

Like the additional selected residues in the recognition strand, all residues of the blocking strand are chosen carefully. The blocking strand is designed to improve overall solubility and create the desired overall formal charge, to promote interstrand interactions with the recognition strand which pre-organize the mimetic into a β-sheet conformation, and to provide other desired structural features (e.g., the flanking residue b1 which helps to provide hydrophobic clustering). The blocking strand is generally about as long as, or longer by 1, 2, or 3 residues, than the recognition strand. In some embodiments, the blocking strand may be longer than the recognition strand, to maximize interstrand interaction and conformational control of the recognition strand, and to provide enough formal charge for a hydrophobic recognition strand to be soluble in aqueous solutions, such as solutions at physiological pH and temperature. In other embodiments, the blocking strand may be the same length, or shorter, particularly when the recognition sequence has sufficient formal charge.

Since the flanking residues $b^1$ and $r^1$ interact hydrophobically and by intramolecular hydrogen bonding (interstrand hydrogen bonding), strands having odd numbers of residues (e.g., 3, 5, 7, or 9) interact approximately as well as the next-higher even number. Amino acids in both strands are either all L-amino acids or all D-amino acids. In some embodiments, the residues may be non-naturally occurring amino acids, amino acid mimetics, or linked by $sp^2$ like amide bond isosteres such as depsi peptides, aryl, aromatic, cyclic, or conjugated alkenylene moieties. Preferably, the blocking strand has a high density of β-branched residues such as valine, leucine, and isoleucine. In some embodiments, the blocking strand can include a recognition sequence.

Selection of interstrand residue pairs ($b^i$ and $r^i$) can promote interstrand interaction. Interactive residue pairs include II, RE, IY, and other pairwise interactions cited in Regan et al. *Science* 1995 270:980–982. According to Regan, interstrand interaction is promoted by the following pairs, listed in order from best to worst: ER, EK, FF, IY, FY, IF, II, IW, FW, IV, FV, FT, and IT.

N-methylation is strategically located on a residue adjacent to an intramolecularly hydrogen-bonded residue. In other words, the N-methylated residue of one strand is pointing towards the solvent, and pointing away from the other strand. Preferably, there is at least one such N-methylated residue in each of the blocking strand and recognition strand. In some embodiments, an N-methylated residue is not a terminal residue. Where a strand is a deca-, bideca- or tridecapeptide, the strand should have at least one N-methylated residue for every 7 or 8 residues, on average.

The β-turn mimic provides conformational control of a polypeptide through hydrophobic clustering and hydrogen bonding between or among residues. In some embodiments, at μM to mM concentrations, N-methylation of certain peptides reduces intermolecular β-sheet formation among the monomeric or dimeric peptidomimetics disclosed herein.

Examples of mimetics are shown in Scheme II. Additional mimetics include: a blocking sequence which further includes amino acids such that the formal charge of said peptidomimetic is between 2.0 and 4.0 at physiological pH, and preferably between 2.5 and 4.0, or 3.0 and 4.0; the blocking strand provides at least one residue $b^i$ which promotes interstrand interaction with a residue $r^i$ of said recognition strand; at least two pairs of residues which promote interstrand interaction, each pair selected independently from the following pairs: ER, EK, FF, IY, FY, IF, II, IW, FW, IV, FV, FT, and IT; each of the first and second N-methylated residues is a non-terminal residue; at least one in every 8 residues is N-methylated; the blocking strand has fewer residues than the recognition strand, e.g., 1, 2, or 3 fewer; the mimetic is cyclic; the mimetic has no more than 12 residues, no more than 6 residues, or no more than 4 residues; the diarylheterocycle has the formula II; the diarylheterocycle has the formula III.

2. Characterization

Peptidomimetics containing the disclosed synthetic reverse-turns can be characterized by methods known to those in the art, including MALDI mass spectrometry, analytical equilibrium ultracentrifugation, N-terminal sequencing, NMR, X-ray diffraction, circular dichroism spectroscopy, and electron microscopy, and FT-IR.

Furthermore, aggregation or fibril formation is demonstrated by methods known to those in the art, such as aggregation assays (Jarrett, J. T., et al., *Biochemistry* 32:4693–4697 1993; and Lai, Z. et al. *Biochemistry* 35:6470–6482 1996), direct and indirect lightscattering assays (e.g., Lomakin A., et al. *Proc. Natl. Acad. Sci. USA* 93:1125–1129 1996), dye-binding of thioflavine S or thioflavine T (e.g., LeVine, H., Amyloid: *Int. J. Exp. Clin. Invest.* 2:1–6 1995), and dye-binding of Congo Red (e.g., Klunk, et al., *J. Histochem.* and *Cytochem.* 37:1273–1281 1980).

Some embodiments provide a pre-organized β-strand conformation that does not aggregate at high peptide concentrations. Transthyretin dissociates from its normal tetrameric state to a monomeric state under mildly acidic conditions (pH 5). The monomeric form, a putative TTR amyloidogenic intermediate that is an antiparallel β-sheet, self-associates into amyloid fibrils. Disclosed synthetic monomeric β-strands such as bind to the monomeric form of TTR, thereby inhibiting TTR amyloid fibril formation in aqueous solutions.

The invention also provides a two-stranded antiparallel β-sheet inhibitor. This inhibitor includes a sequence on one strand designed to bind the amyloidogenic intermediate and one or more N-methylated residues on the other strand which prevent the TTR amyloidogenic intermediate from self-associating and forming intermolecular β sheets.

SCHEME II

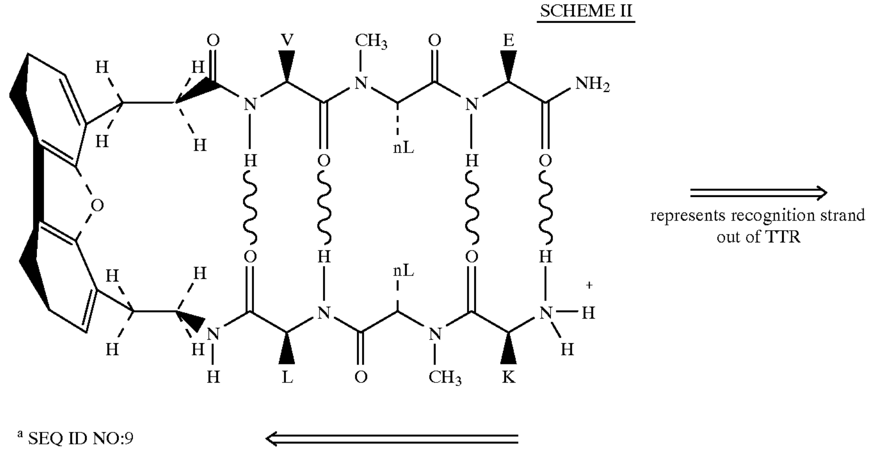

[a] SEQ ID NO:9

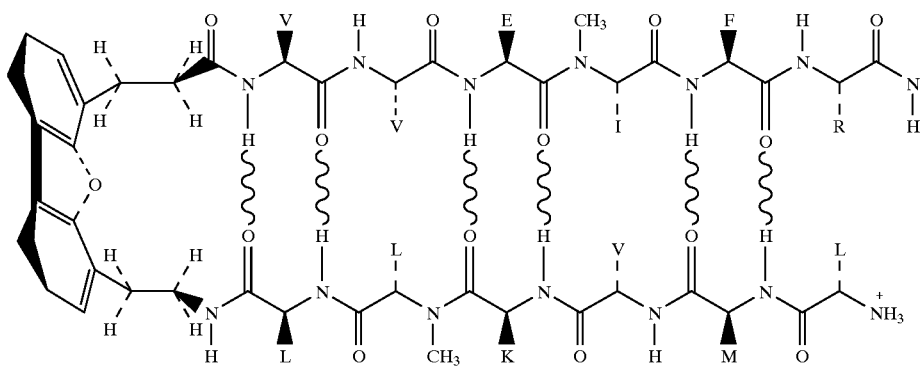
a SEQ ID NO:10
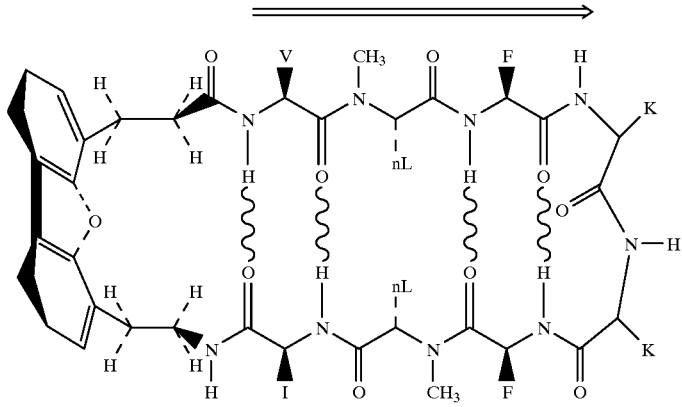
a SEQ ID NO:11
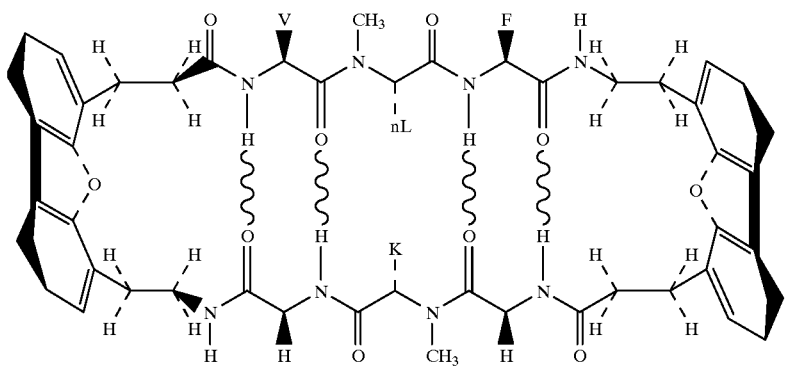
a SEQ ID NO:12

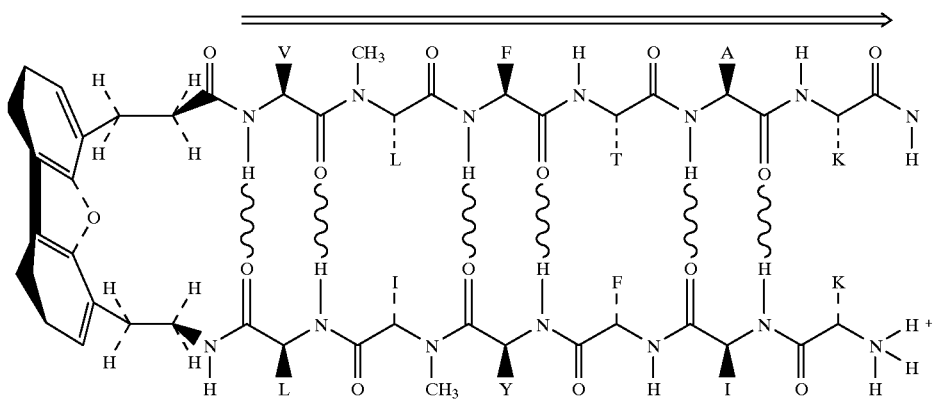
[a] SEQ ID NO:13
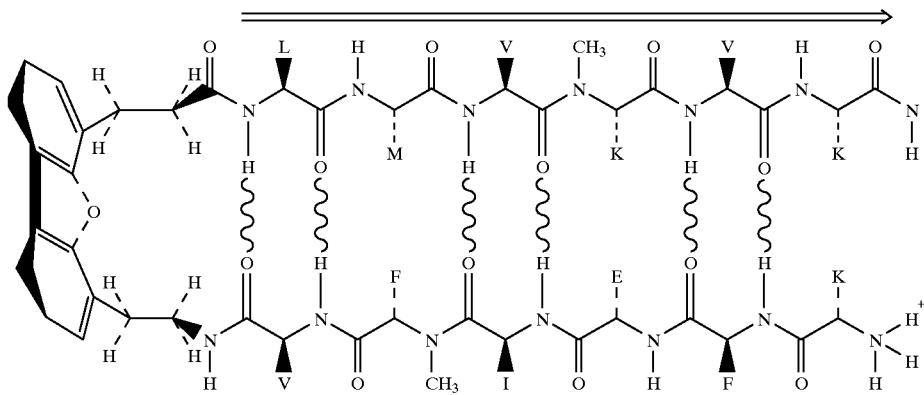
[a] SEQ ID NO:14
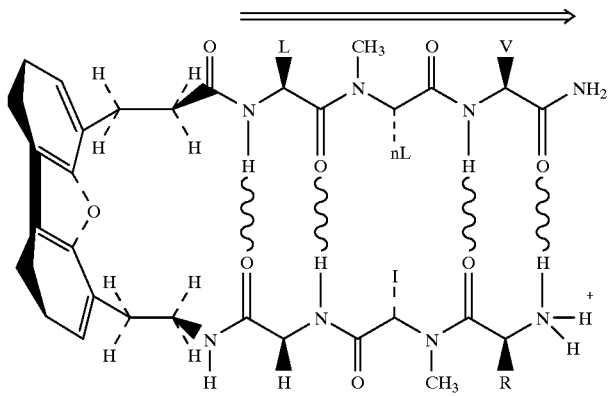
[a] SEQ ID NO:15

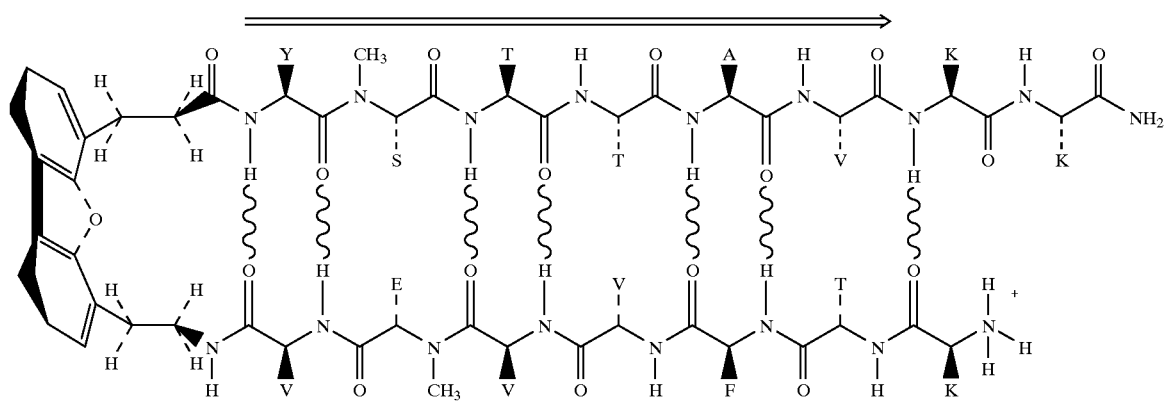
[a] SEQ ID NO:16
(two recognition strands for binding to a β-sandwich protein like TTR)
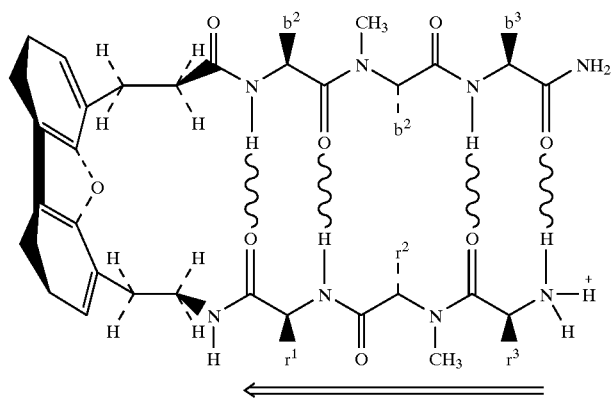

-continued
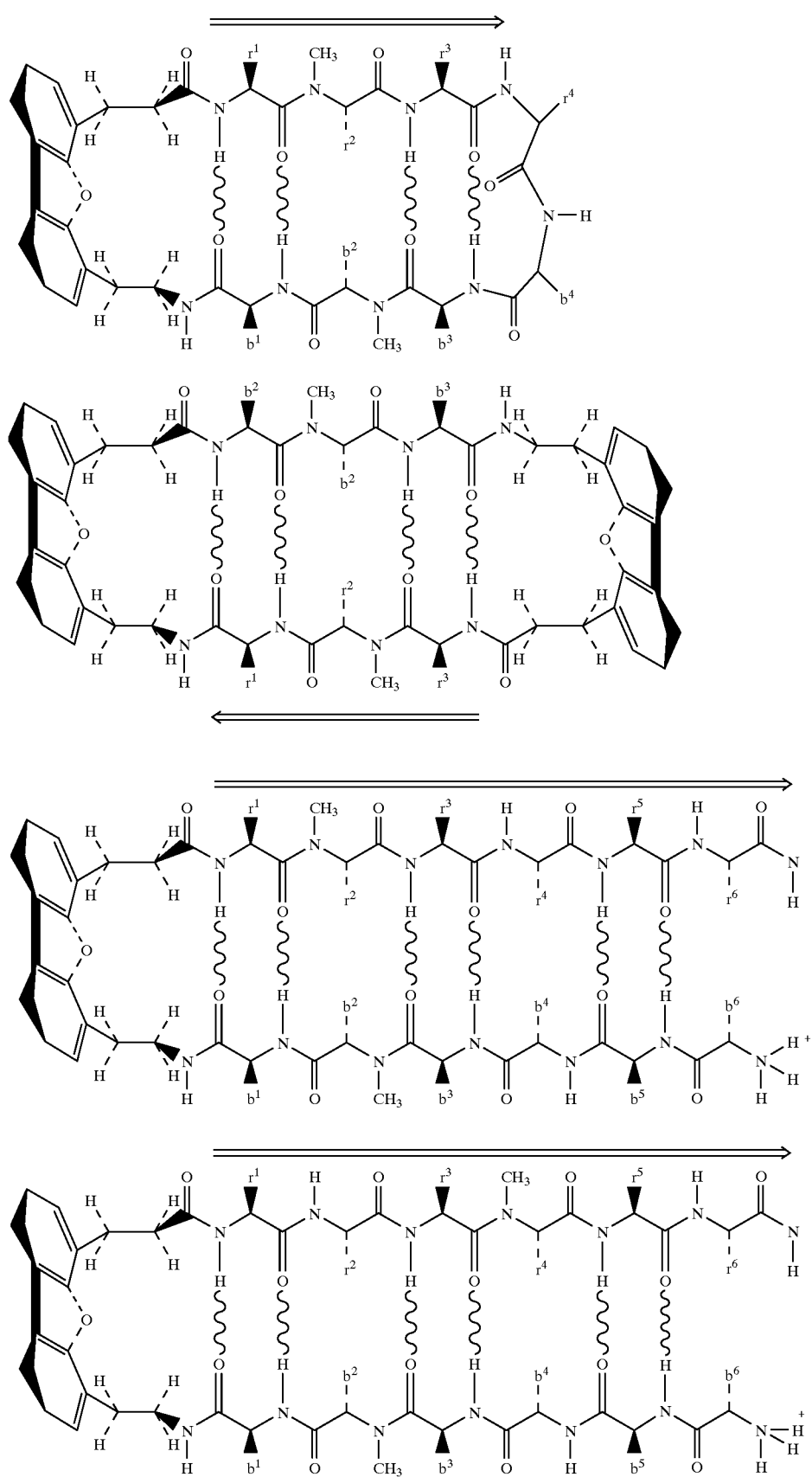

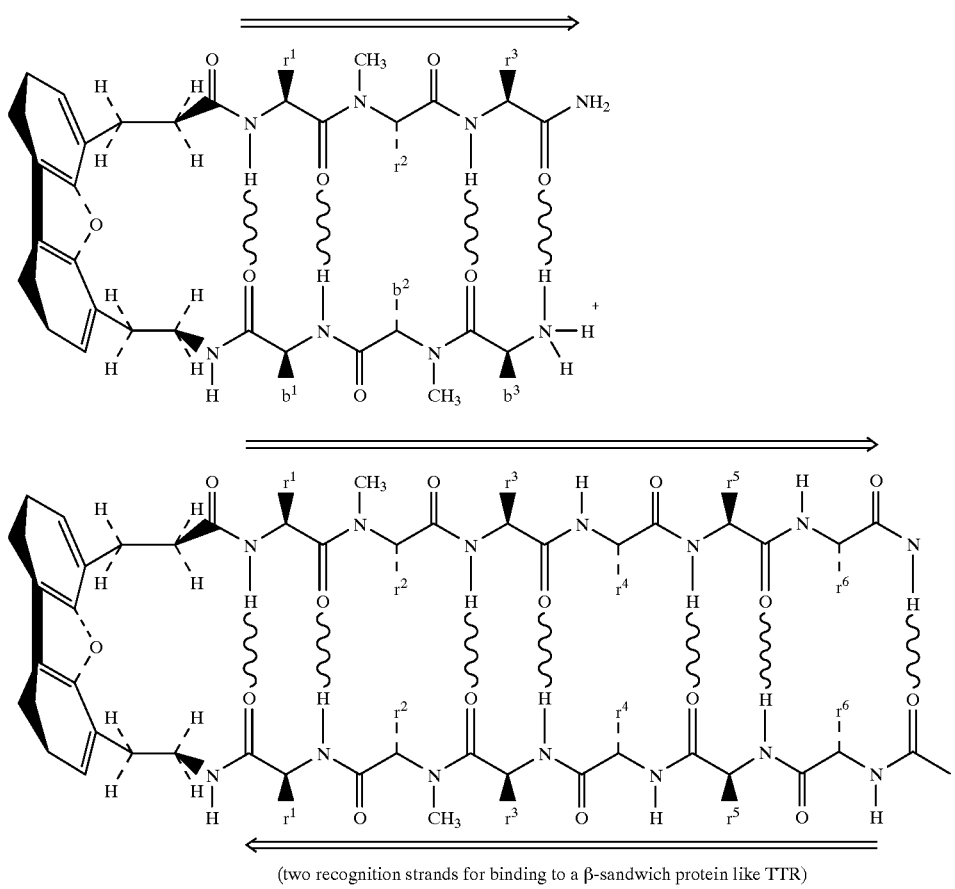

(two recognition strands for binding to a β-sandwich protein like TTR)

E. Use

The mimetics disclosed herein which inhibit intermolecular aggregation can be used as therapeutics for any disease or condition that is mediated by a protein which requires assembly, such as self-assembly of dimeric or oligomeric forms for activity (e.g., enzymatic activity). One aspect of the invention therefore features a method of inhibiting amyloid protein assembly, including exposing an aqueous solution of amyloid protein at physiological temperature and pH to a peptidomimetic of the invention. One embodiment further includes measuring the extent of amyloid protein assembly. Other embodiments of this aspect feature inhibiting a β-sheet mediated condition in a mammal (e.g., a human), such as viral infection, HIV infection, or Alzheimer's disease or symptoms associated therewith. Thus the invention provides a method of treating an cross-β amyloid fibril-mediated disease, including administering to a patient in need of such treatment an effective amount of a peptidomimetic of the invention and a pharmaceutically acceptable carrier.

Cross-β amyloid fibril-mediated diseases include Alzheimer's disease, primary systemic amyloidosis, senile systemic amyloidosis, familial amyloid polyneuropathy I, hereditary cerebral amyloid angiopathy, hemodialysis-related amyloidosis, familial amyloid polyneuropathy III, Finnish hereditary systemic amyloidosis, Type II diabetes, medullary carcinoma of the thyroid, spongiform encephalopathy, atrial amyloidosis, hereditary non-neuropathic systemic amyloidosis, injection-localized amyloidosis, and hereditary renal amyloidosis.

Corresponding precursor proteins (and fibril components) are, respectively: β protein (β protein 1-40, 1-41, 1-42, 1-43), immunoglobin light chain (intact light chain or fragments thereof), serum amyloid A (amyloid A (76 residue fragment), transthyretin (transthyretin or fragments thereof), transthyretin (over 45 transthyretin variants), cystatin C (cystatin C minus 10 residues), $\beta_2$-microglobulin (same), apolipoprotein A-1 (fragments thereof), gelsolin (71 amino acid fragment thereof), Islet amyloid polypeptide or IAPP (fragment of IAPP), calcitonin (fragments thereof), prion (prion or fragments thereof), atrial natriuretic factor or ANF (same), lysozyme (lysozyme or fragments thereof), insulin (same), and fibrinogen (fragments thereof). Recognition sequences are preferably selected from the fibril component. However, methods known to those in the art such as alanine scanning can be used to identify particular recognition sequences.

This method includes administering an effective amount of a pharmaceutical composition containing a peptidomimetic disclosed herein and a pharmaceutically acceptable carrier; or administering a peptidomimetic including a blocking strand containing an N-methylated residue and a residue selected from histidine and hydrophobic residues, a recognition strand containing an N-methylated residue and a residue selected from histidine and hydrophobic residues, and a natural or synthetic β-turn, which is linked to both the blocking strand and the recognition strand. The pharmaceutical compositions can be formulated variously as solutions, tablets, capsules, or implants, solutions being preferred. The attending physician will be able to determine what an effective dosage would be for a given patient, based on factors such as age, general health, weight, and the extent of the disease or condition to be treated.

Another aspect of the invention features a method of inhibiting intramolecular β-structure dependent protein assembly, including exposing a target protein to a peptidomimetic of the invention. The protein can be in solution, in fibrillar form, or in crystalline form. In one embodiment, the target protein requires monomeric form for function, and is thereby stabilized. In another embodiment, the target protein requires dimeric or oligomeric form for function, and its function is thereby inhibited. In some embodiments, inhibition of protein assembly is useful for storage or analysis of a protein. Similarly, the invention includes a method of inhibiting amyloid protein assembly, comprising exposing an aqueous solution of amyloid protein at physiological temperature to a disclosed peptidomimetic. In some embodiments, the aqueous solution has a pH between 5.0 and 7.5; or the method further includes, after the exposing step, the step of measuring the extent of amyloid protein assembly.

Another aspect of the invention features a method of down-regulating a target peptide (e.g., a hormone such as somatostatin), including administering to a patient an effective amount of a pharmaceutical composition containing a peptidomimetic of the invention containing a recognition sequence of the target peptide. One embodiment of this method reduces the incidence of interaction between the peptide and its receptor by interfering with peptide-receptor recognition.

Another aspect of the invention features a method of imaging a target protein (e.g., a fibril, a fibril-forming peptide, or another a peptide having β-structure) in vivo, including administering a detectable label (e.g., radiolabel or fluorescent label) containing a peptidomimetic of the invention having a recognition sequence derived from the target protein to a patient, and detecting said label. One embodiment of this method distinguishes between active (e.g., functional or pathological) conformations or assemblies and inactive or precursor conformations.

Another aspect of the invention features a monoclonal antibody to a peptidomimetic of the invention, or to a peptidomimetic-target protein conjugate. The antibody may be polyspecific or monospecific. Such an antibody is useful as a diagnostic reagent (in a method for detecting self-assembled peptides, aggregated peptides, or fibrillar peptides) or as a research tool.

Without further elaboration, it is believed that the present invention can be utilized to its fullest extent. The following examples are therefore to be construed as illustrative of the remainder of the disclosure.

EXAMPLES

Unless otherwise noted, materials were obtained from commercial suppliers and were used without further purification. Tetrahydrofuran (THF) and diethyl ether (Et2O) were distilled from sodium/benzophenone ketyl under nitrogen (N2). The concentration of n-BuLi was determined by titration. Trimethylsilyl chloride (TMSCl), was distilled from calcium hydride under N2. Triethylamine (TEA) and N,N,N',N'-tetramethylethylenediamine (TMEDA) were refluxed over ninhydrin, distilled, and then redistilled from calcium hydride or potassium hydroxide. Routine $^1$H NMR and $^{13}$C NMR spectra were recorded on a Varian XL-200E spectrometer and are reported in parts per million (d) relative to $CHCl_3$ (7.24 ppm). Analytical thin layer chromatography was performed on E. Merck silica gel 60 F254 plates. Column chromatography was performed as described by Still 12 using forced flow (flash) chromatography with the indicated solvents on Baxter SIP silica gel 60% (230–400 mesh). Melting points were obtained on a Bristoline apparatus and are uncorrected. Nominal resolution mass spectra were obtained on a Hewlett Packard 5971 mass spectrometer and high resolution mass spectra were obtained on a VG-70S double focusing high resolution mass spectrometer. Preparative HPLC was carried out on a dual pump system equipped with Altex 110A pumps and a 420 gradient programmer or a Waters 600 preparative HPLC. Waters RCM Delta Pak C18 and C4 (15=|m, 300%, 25×100 mm) columns and a Knauer 86 variable-wavelength detector were used. Solvent A was composed of 95% water, 5% acetonitrile and 0.2% TFA. Solvent B was composed of 5% water, 95% acetonitrile and 0.2% TFA. Unless otherwise noted, all reactions were run under Argon or Nitrogen.

Example 1

Ethyl-6-propionic acid-4-dibenzofuranpropionate (3)

A 50 mL hydrogenation bottle was charged with ethyl-6-acrylic acid-4-dibenzofuranacrylate (0.23 g, 0.68 mmol) in a 1:1 mixture of ethanol and acetic acid (28 mL). The $PtO_2$ catalyst (7.8 mg, 0.03 mmol, 5 mol %) was added and the mixture was hydrogenated at 13 psi $H_2$ for 6.5 h. The catalyst was removed by filtration through a nylon membrane and the solvents were removed under reduced pressure. The resulting pale yellow solid was dissolved in ether (50 mL) and washed with $H_2O$ (2×30 mL). The organic layer was dried over $MgSO_4$, concentrated under reduced pressure and further dried under high vacuum to afford the saturated monoacid monoester (0.22 g, 94%) as a white solid: mp 92–93° C., $^1$H NMR (d6-acetone) d 10.65 (bs, OH), 7.92 (dd, Jo=7.4, Jm=1.5, 2H, Ar H1 and H9), 7.39 (m, 2H, Ar H3 and H7), 7.30 (m, 2H, Ar H2 and H8), 4.07 (q, J=7.1, 2H, —$CO_2CH_2CH_3$), 3.31 (t, J=7.6, 4H, —$CH_2CH_2CO_2H$ and —$CH_2CH_2CO_2Et$)), 2.85 (m, 4H, —$CH_2CH_2CO_2H$ and —$CH_2CH_2CO_2Et$), 1.16 (t, J=7.1, 3H, —$CO_2CH_2CH_3$); $^{13}$C NMR ($CD_3Cl$) d 178.91, 173.28, 154.38, 127.17, 127.12, 124.67, 124.30, 124.18, 122.89, 119.01, 118.90, 80.63, 34.28, 33.95, 25.48, 25.23, 14.19; MS +FAB (NBA) m/z 340.1333, [M+H]+ calcd for $C_2OH_2O_5$ 340.1311.

4-Trimethylsilyldibenzofuran (4)

An oven-dried, 1 L three-necked, round-bottomed flask was cooled under Ar and charged with dibenzofuran (21.8 g, 129.6 mmol) in freshly distilled THF (260 mL). The flask was fitted with an oven-dried condenser and addition funnel and the system was flushed with Ar. The clear solution was cooled to 0÷C and n-BuLi (97.5 mL of a 1.6 M hexanes solution, 156.0 mmol) was added dropwise over 50 minutes. The resulting dark orange solution was stirred at room temperature for 5 hours and then cooled to 0° C. Addition of TMSCl (32.8 mL, 258.4 mmol) in THF (33 mL) over 5 minutes resulted in the solution becoming yellow. The reaction mixture was stirred at room temperature for 20 minutes (during which time it became cloudy), refluxed for 2 hours, and then stirred at room temperature overnight. The reaction mixture was poured into 250 g crushed ice and stirred. The mixture was then transferred to a separatory funnel and diluted with ether (100 mL). The aqueous layer was extracted with ether (3×75 mL). The combined organic layers were dried over $MgSO_4$, concentrated under reduced pressure and further dried under high vacuum to afford 31.62 g (99%) of a pale yellow oil which was determined by GCMS and HPLC to contain a 95:5 ratio of 4-trimethylsilyldibenzofuran:4,6-ditrimethylsilyldi- benzofuran. The mixture was used in the subsequent iodination reaction without further purification: $^1$H NMR (d6-acetone)

d 8.13–8.07 (m, 2H, Ar H's), 7.69–7.32 (m, 5H, Ar H's), 0.46 (s, 8H, —Si(CH$_3$)$_3$); $_{13}$C NMR (d6-acetone) d 133.79, 128.43, 124.00, 123.11, 122.02, 112.70, –0.07; EIMS m/z 240.0972, M+ calcd for C$_{15}$H$_{16}$OSi 240.0970.

4-Iodo-6-trimethylsilyldibenzofuran (5)

To a solution of 4-trimethylsilyldibenzofuran (4) (7.93 g, 33.0 mmol) in dry diethyl ether (70 mL) and TMEDA (7.97 mL, 52.8 mmol) cooled in an ice-water bath was slowly added n-BuLi (33.0 mL of 1.6 M solution in hexanes, 52.8 mmol) via a syringe. The resulting dark brown solution was stirred at room temperature for 5.5 hours. In a separate oven dried, 500 mL round bottom flask, I$_2$ (19.2 g, 75.9 mmol) was dissolved in dry Et$_2$O (70 mL) and cooled to –78° C. in an acetone-dry ice bath. The dibenzofuran anion was then slowly canulated into the stirring I$_2$ solution. The resulting brown mixture was allowed to warm to room temperature while stirring overnight. The mixture was transferred to a cold (0° C.) solution of 20% NaHSO$_3$ (~500 mL) and stirred vigorously. It was diluted with CH$_2$Cl$_2$ (~200 mL) and additional solid NaHSO$_3$ was added until the mixture became pale yellow. Vigorous stirring was continued for 2.5 hours. The layers were separated and the aqueous layer was extracted with CH$_2$Cl$_2$ (2×100 mL). The combined organic layers were extracted with 20% NaHSO$_3$ (2×150 mL), dried over magnesium sulfate and concentrated under reduced pressure to give a pale yellow solid. Dissolving the yellow solid in hexanes allowed separation of the compound from a brown, gummy, insoluble impurity. The hexane solution was decanted and concentrated under reduced pressure to give 12.5 g of compound (5). The crude material in hexanes (35 mL) was filtered through a silica gel column using hexanes (~300 mL) as eluant. In this filtration only two 125 mL fractions were collected (t.l.c. rf=0.45 in hexanes). Since the second fraction appeared slightly yellowish, the two fractions were analyzed separately and combined later to give 8.57 g of a cream colored solid (75% based on 95% monosilylated dibenzofuran in the starting material). The melting points for the first and second fractions were 62–69° C. and 71–78° C., respectively. However, the two fractions were identical by $_1$H-NMR and HPLC. An analytical sample was obtained after purification by preparative C4 HPLC as a white solid: mp 74–77° C.; $_1$H NMR (CD$_3$Cl) d 7.92 (dd, Jo=7.6, Jm=1.4, 1H, Ar H3), 7.90 (dd, Jo=7.6, Jm=1.5, 1H, Ar H7), 7.79 (dd, Jo=7.8, Jm=1.1, 1H, Ar H1), 7.56 (dd, Jo=7.2, Jm=1.4, 1H, Ar H9), 7.35 (t, Jo=7.6, 1H, Ar H8), 7.09 (t, Jo=7.7, 1H, Ar H2), 0.50 (s, 7H, —Si(CH$_3$)$_3$); $_{13}$C NMR (CD$_3$Cl) d 156.33, 150.04, 135.47, 132.91, 124.39, 124.12, 123.50, 122.94, 122.88, 122.03, 120.47, –1.06; EIMS m/z 365.9877, M+ calcd for C$_{15}$H$_{15}$OISi 365.9939 and 350.9676, [M–CH3]+ calc 350.9704.

Ethyl-6-trimethylsilyl-4-dibenzofuranacrylate (6)

An oven-dried, 100 mL round-bottomed flask was cooled under Ar and charged with 4-iodo-6-trimethylsilyldibenzofuran (5) (3.82 g, 10.4 mmol), palladium acetate (49.2 mg, 2.1 mol %), and tri-ortho-tolylphosphine (0.162 g, 5.1 mol %). The flask was fitted with a condenser and the system was alternately evacuated under high vacuum and flushed with Ar (4 cycles). Acetonitrile (16.5 mL), triethylamine (4.36 mL, 31.1 mmol), and ethyl acrylate (3.39 mL, 31.3 mmol) were added through the condenser and the mixture was heated to 85÷C in an oil bath. The reaction mixture was cooled to room temperature when the palladium precipitated after 2 hours. The mixture was concentrated under reduced pressure to give a yellow-brown solid which was then partitioned between CH$_2$Cl$_2$ (120 mL) and H$_2$O (150 mL). The aqueous layer was extracted with CH$_2$Cl$_2$ (3×75 mL). The combined organic layers were dried over MgSO$_4$ and concentrated under reduced pressure. The crude material was purified by flash chromatography (95:5 hexanes:ethyl acetate) to afford the pure compound (3.27 g, 93%) as an oil which solidified upon standing to afford beige solid: mp 48–52° C.; $^1$H NMR (d6-acetone) d 8.16 (d, Jo=7.6, 2H, Ar H1 and H9), 7.98 (d, J=16.2, 1H, —CHCHCO$_2$Et), 7.77 (dd, Jo=7.0, Jp=0.6, 1H, Ar H3), 7.64 (dd, Jo=7.2, Jm=1.3, 1H, Ar H7), 7.44 (td, Jo=7.6, Jm=1.6, 2H, Ar H2 and H8), 7.20 (d, J=16.2, 1H, —CHCHCO$_2$Et), 4.28 (q, J=7.1, 2H, —CO$_2$CH$_2$CH$_3$), 1.34 (t, J=7.1, 3H, —CO$_2$CH$_2$CH$_3$), 0.52 (s, 8H, —Si(CH$_3$)$_3$); $^{13}$C NMR (d6-acetone) d 167.51, 139.99, 134.60, 134.32, 129.78, 126.14, 124.59, 124.55, 124.08, 123.89, 123.36, 123.25, 122.98, 120.74, 61.27, 14.99, –0.56; EIMS m/z 338.1349, M+ calcd for C$_{20}$H$_{22}$O$_3$Si 338.1338.

Ethyl-6-iodo-4-dibenzofuranacrylate (7)

A flame-dried, 1 L round-bottomed flask was cooled under Ar and charged with ethyl-6-trimethylsilyl-4-dibenzofuranacrylate (6) (11.37 g, 33.6 mmol), anhydrous K$_2$CO$_3$ (14.22 g, 102.9 mmol), and anhydrous CCl$_4$ (230 mL). The solution was allowed to cool to 0° C. The ICl (5.0 mL, 95.5 mmol) was transferred via a teflon canula to a septum capped graduated cylinder which had been flame-dried under Ar and charged with anhydrous CCl$_4$ (34 mL). The resulting 2.8 M solution was then transferred to the cold reaction flask via the teflon canula. The graduated cylinder and canula were rinsed with an additional 5 mL portion of CCl$_4$. The red wine colored solution was allowed to warm to room temperature and stirred in darkness overnight. The reaction mixture was poured into 500 mL of a 20% Na$_2$S$_2$O$_3$ solution and vigorously stirred. Additional solid Na$_2$S$_2$O$_3$ was added and the mixture was stirred until very pale yellow. The mixture was transferred to a separatory funnel and the layers were separated. The aqueous layer was extracted with CH$_2$Cl$_2$ (3×200 mL). The combined organic layers were washed with 20% Na$_2$S$_2$O$_3$ (3×500 mL), 10% HCl (2×500 mL), 1N NaOH (3×500 mL), and H$_2$O (1×500 mL). The colorless organic layer was then dried over MgSO$_4$ (solution became pale pink) and concentrated in vacuo to give 16.60 g of beige solid. After further drying under high vacuum, the solid was crushed and stirred in a minimal amount of hexanes and ethyl acetate solution (95:5) for 2 hours. This resulted in the removal of the pink color and isolation of a white solid. Drying under high vacuum afforded 12.5 g (95%) of white solid: mp 114–116° C.; $^1$H NMR (d6-acetone) d 8.15 (dd, Jo=7.7, Jm=1.1, 1H, Ar H8), 8.14 (dd, Jo=7.7, Jm=1.1, 1H, Ar H7), 7.96 (d, J=16.1, 1H, —CHCHCO$_2$Et), 7.95 (d, Jo=7.8, 1H, Ar H9), 7.82 (dt, Jo=7.7, Jp=0.6, 1H, Ar H1), 7.48 (t, Jo=7.6, 1H, Ar H3), 7.25 (t, Jo=7.7, 1H, Ar H2), 7.15 (d, J=16.1, 1H, —CHCHCO$_2$Et), 4.29 (q, J=7.1, 2H, —CO$_2$CH$_2$CH$_3$), 1.34 (t, J=7.1, 3H, —CO$_2$CH2CH3); $^{13}$C NMR (d6-acetone) d 167.52, 150.05, 139.50, 137.77, 130.41, 126.59, 126.48, 125.21, 125.03, 124.50, 123.40, 122.41, 121.02, 76.29, 69.67, 61.38, 15.04; MS +FAB (NBA) m/z 393.0001, [M+H]+ calcd for C$_{17}$H$_{13}$O$_3$I 392.9988.

Ethyl-6-acrylic acid-4-dibenzofuranacrylate (8)

An oven-dried, 50 mL round bottom flask was charged with ethyl-6-iodo-4-dibenzofuranacrylate (7) (2.60 g, 6.63 mmol), palladium acetate (32.8 mg, 2.2 mol %), and tri-ortho-tolylphosphine (101.9 mg, 5.0 mol %) and the flask was fitted with an oven-dried condenser. The system was alternately evacuated under high vacuum and purged with Ar (4 cycles). The acetonitrile (12 mL), triethylamine (3.25 mL, 23.2 mmol), and acrylic acid (1.5 mL, 19.9 mmol) were added via syringe through the condenser. The resulting dark brown mixture was heated to 85÷C in an oil bath. The reaction mixture was cooled to room temperature after 4 hours when the palladium precipitated. After removal of solvent under reduced pressure, the mixture was taken up in CH2Cl2 (100 mL) and washed with H2O (75 mL). The aqueous layer was extracted with CH2Cl2 (4*50 mL). The combined organic layers were dried (MgSO4) and concentrated under reduced pressure to give a yellow solid. Purification by flash chromatography (70:29:1 hexanes:ethyl acetate: acetic acid to 60:40 hexanes ethyl acetate) afforded 1.64 g (74%) of a yellowish white solid: mp 184–187÷C; 1H NMR (d6-acetone) d 8.28 (dd, Jo=7.7, Jm=1.1, 2H, Ar H1 and H9), 8.05 (d, J=16.3, 2H, —CHCHCO2H and —CHCHCO2Et), 7.86 (dd, Jo=7.6, Jp=0.6, 2H, Ar H3 and H7), 7.51 (td, Jo=7.6, Jm=1.1, 2H, Ar H2 and H8), 7.08 (d, J=16.2, 1H, —CHCHCO2H), 7.07 (d, J=16.1, 1H, —CHCHCO2Et), 4.28 (q, J=7.1, 2H, —CO2CH2CH3), 1.35 (t, J=7.1, 3H, —CO2CH2CH3); 13C NMR (d6-acetone) d 172.45, 159.70, 154.43, 144.13, 143.57, 134.22, 133.95, 130.08, 129.65, 128.49, 127.52, 127.40, 125.39, 65.82, 59.72, 19.37; MS +FAB (NBA) m/z 337.1080, [M+H]+ calcd for C20H16O5 337.1077.

4-(2-t-butyloxycarbamylethyl)-6-dibenzofuranethyl propenoate (9)

See Tsang, K. Y.; Diaz, H.; Graciani, N.; Kelly, J. W. J. Am. Chem. Soc. 1994, 116:3988 for detailed procedure. 4-(2-9-fluorenylmethyloxycarbamylethyl)-6-dibenzofuranethyl propenoate (10).

An oven-dried 50 mL round bottom flask cooled in a desiccator over calcium sulfate (Drierite) was charged with 0.18 g (0.44 mmol) of 9. The flask was held under vacuum for 2 hours, after which the flask was equipped with a stir bar and 20 mL of a 30% by volume solution of trifluoroacetic acid in dichloromethane. After stirring for 50 minutes at room temperature, the $CH_2CL_2$/TFA was removed under aspirator vacuum, and replaced with 20 mL of $CH_2CL_2$, and 0.500 g of $Na_2CO_3$. The mixture was stirred at room temperature for 10 minutes to allow for complete neutralization of any remaining TFA, upon which 0.200 g (2.5 equiv.) of FMOC-OSu was added. This mixture was stirred at room temperature overnight, followed by removal of $Na_2CO_3$ by filtration through a 45 micron nylon membrane, and $CH_2Cl_2$ under aspirator vacuum. The resulting oil was purified by flash chromatography (70:30, hexans:ethyl acetate) to give 0.180 g (77% yield) of a white solid of 10. $C_{34}H_{31}NO5$ calc'd [M+H]=534.2281 found [M+H]= 534.2287 1H NMR (CDCl3) δ1.18 (t,3H), 2.79 (t,2H) 3.22 (t,2H), 3.31 (t,2H), 3.68 (t,2H,), 4.1 (m,3H), 4.36 (d,2H), 5.05 (t,1H), 7.24 (m,6H), 7.37 (t,2H), 7.51 (d,2H),7.73 (d,2H), 7.82 (m,2H).

Example 2

Preparation of Boc-Leu-2-CO₂H (3) for Incorporation into Peptide E.

Methyl 2-amino-3'-biphenylcarboxylate[7] (176.7 mg, 0.78 mmol) was dissolved in CH₂C/DMF (20 mL of a 9;1 mixture) in a 50 mL round-bottomed flask. To the dark yellow solution were added Boo-Leu-H₂O (1.94 g. 7.78 mmol), DIEA (1.70 mL, 9.76 mmol), and BOP reagent (3.51 g. 7.94 mmol). The reaction mixture was stirred at room temperature under N₂ for 42 h. N,N'-Dimethylethylenediamine (1.7 mL, 16 mmol) was added, and the mixture was stirred for 2 h to destroy the excess HOBt active ester. The reaction mixture was transferred to a separatory funnel and washed with 1 M citric acid (3×25 mL), 5% HaHCO₂ (2×35 mL), and H₂O (50 mL). The organic layer was dried (MgSO₄), concentrated in vacuo, and further dried under high vacuum to afford a beige solid.

The crude material was dissolved in anhydrous MeOH (50 mL), and NaOH was added (13.0 mL of a 0.59 M solution in MeOH, 7.7 mmol). The clear yellow solution was heated at reflux for 72 h. The reaction mixture was concentrated, and the yellow residue was partitioned between CH₂Cl₂ and H₂O (100 mL each). The aqueous layer was washed with CH₂Cl₂ (3×100 mL). The combined organic layers were washed with H₂O (100 mL), dried (MgSo₄), concentrated in vacuo, and further dried under high vacuum to afford 1.37 g of a light yellow residue. The material was purified by flash chromatography (70:30 to 50:50 hexanes/ethyl acetate) to afford 0.302 g (89%) of a white solid; MALDI-γOFMS (MH⁻) in/z calcd 427.2, obsd 427.7; MS (+FAB, NBA/ PEGH) in/z 127.2237, [M+H]⁻calcd for $C_{24}H_{30}OsN_2$, 427.2233.

Synthesis of Peptides A–G. Manual solid phase peptide synthesis was carried out using the benzhydrylamine resin available from Advanced Chemtech. The resins used had a loading of 0.70 or 0.55 mequiv/g. Reagent grade dichloromethane, isopropyl alcohol (IPA) and N,N-dimethylformamide (DMF) were used. DMF was stored over 4 A molecular sieves. Side chain protected Boo-amino acids were purchased from Advanced Chemtech. Trifluoroacetic acid (TFA) was purchased from Solvay Performance Chemicals and was used as a 35% solution in CH₂Cl₂ containing 1% thioanisole as a scavenger. N,N-Diisopropylethylamine (DIEA) was refluxed over ninhydrin, distilled, and then distilled from calcium hydride. The first amino acid was loaded onto the resin by shaking 1.6 equiv of the diisopropylcarbodiimide-activated amino acid with the resin for 24 h. The resin was washed with DMF (2×1 min), IPA (1×1 min., CH₂Cl₂ (1×1 min), IPA (1×1 min), CH₂Cl₂ (1×1 min), IPA (1×1 min), and CH₂Cl₂ (4×1 min). The Kaiser ninhydrin test was used to monitor completion of all couplings. If the test was slightly positive, the unreacted amino groups were acetylated with acetic anhydride or the peptide was recoupled. Standard couplings were performed in the following manner: TFA prewash (35% TFA×1 min). TFA deprotection (35% TFA×50 min), CH₂Cl₂ (2×1 min), IPA (1×1 min), CH₂Cl₂ (1×1 min) IPA (1×1 min), CH₂Cl₂ (4×1 min), preneutralization (12% DIEA×1 min), neutralization (12% DIEA×9 min), CH₂Cl₂ (4×1 min), coupling (3 equiv of amino acid, 3 equiv of BOP, 4 equiv of DIEA in CH₂Cl₂ containing 10–15% DMF for 2–8 h), DMF (2×1 min), IPA (1×1 min), CH₂Cl₂ (1×1 min), IPA (1×1 min), CH₂Cl₂ (1×1 min), IPA (1×1 min), CH₂Cl₂ (4×1 min). The dipeptide Boo-Leu-2—CO₂H (3) was incorporated into peptide E by shaking the preneutralized resin with 1.8 equiv of 3, 2 equiv of BOP, and 3.2 equiv of DIEA in CH₂Cl₂ containing 10–15% DMF for 15 h. The Boc-protected analogue of amino acid 1 (3'-[2-[N-(tert-butyloxycarbonyl) amino]ethyl]-2-bephenylpropionic acid, compound 4)[7] was incorporated into peptides A–D, F, and G by shaking 0.6–3.0 equiv of preneutralized resin with 1.0 equiv of 4, 1.1. equiv of BOP, and 1.4 equiv of DIEA in CH₂Cl₂ containing 10–15% DMF for 40–66 h. Peptide G was subjected to three valine couplings (6 equiv of valine, 6 equiv of BOP. 8 equiv of DIEA) after incorporation of each of the N-methylleucine residues. The resin was then capped with acetic anhydride, and subsequent couplings were performed as described above. Upon completion, the resin-bound peptides were treated with TFA to remove the Boc group, dried under high vacuum, and treated with HF[16] to deprotect the side chains and cleave the peptide from the resin. The crude peptides were purified by preparative C₁₈ HPLC. All peptides were characterized by matrix-assisted laser desorption ionization time-of-flight mass spectrometry (MALDI-γOFMS).

Circular Dichroism Studies of Peptides A–F. Residue 1A was incorporated into three heptapeptide sequences based on the cyclic peptide Gramicidin S. One of the two D-Phe-Pro dipeptide units (the i+1 and i+2 dipeptides of the two β-turns) of Gramicidin S was replaced by residue 1A while the other was omitted from the sequence, affording an acyclic peptide. Heptapeptide A has an -amino acid sequence homologous to a 4-(2-aminoethyl)-6-dibenzofuranpropionic acid-based heptapeptide studied previously, allowing comparsion of the efficacy of the biphenyl- and dibenzofuran-based amino acids as nucleators in a momologous α-amino acid sequence. Peptide B, having a Phe in place of Leu-3, was prepared to test the feasibility of using an aromatic-aromatic interaction to stabilize the hydrophobic cluster and facilitate β-sheet folding. In peptide C, ornithine-2 was replaced with Glu to probe the effect of an addition long-range residue-residue electrostatic interaction (salt bridge) on β-sheet stability in the context of a heptapeptide. Evaluation of peptides A and B by far-UV circular dichroism (CD) reveals that these peptides exist as a random coil in aqueous solution over a pH range of 4–9. The CD spectra exhibit minima at 200 nm, consistent with a rapidly interconverting ensemble of conformations. The analogous 4-(2-aminoethyl)-6-dibenzofuranpropionic acid-based heptapeptides exhibit fluctuating β-sheet structures under these conditions. Peptide C adopts a random coil structure at pH 5 (minimum 201 nm). However, at pH 7, a coil to soluble associated β-sheet transitions observed as discerned from a CD maximum at 193 nm and a minimum at 214 nm. Most likely deprotonation of Glu-2 allows the formation of both intramolecular and intermolecular salt bridges which contribute to the added stability of this β-sheet quaternary structure (vide infra). As expected, the intramolecular folding and the self-association equilibria are linked as discerned from the observation of an insoluble β-sheet structure at pH values >7.5 (peptide concentration of 0.25 mM).

The tridecameric peptides D–F were studied by far-UV CD to determine whether the incorporation of 1A and 2A into longer amphiphilic peptides would result in β-sheet folding. These sequences are similar to the repeating (Val-Lys)$_n$ sequential polypeptides (n>25) which are known to undergo a coil to self-associated β-sheet transition at pH 8.9. The high charge density on peptides D and E should prevent the favorable strand-strand interactions required for sheet formation at low pH. The removal of two or more of the charges on the Lys ε-ammonium groups effected by increasing the pH is expected to facilitate intramolecular folding followed by self-assembly. A leucine was employed as one of the flanking residues in these peptides instead of valine because the increased side chain flexibility should maximize packing interactions required for hydrophobic cluster formation. Interestingly, peptide D undergoes a marked transition from a random coil (minimum at 203 nm) to a β-sheet (maximum at 201 nm, minimum at 214 nm) from pH 8.6 to pH 9.0. The folding transition from a random coil to a β-sheet exhibited by peptide D appears to be a simple two-state transition, as implied by the isodichroic point at 207 nm in the pH dependent far-UV CD spectra. However, the linear concentration dependence of the far-UV CD spectra of peptide D suggested that it underwent self-association subsequent to intramolecular folding. Peptide D existed as a mixture of random coil and β-sheet structures at concentrations below 0.075 mM and as a self-associated β-sheet over the concentration range of 0.075–0.15 mM (pH 9.3). These results and those for peptide C imply that self-assembly significantly stabilizes the metastable intramolecularly folded β-sheet state (vide infra), implying that 1A is capable of nucleating intramolecular β-sheet folding in appropriate sequences. Peptide E was identical to peptide D except that it incorporated residue 2A in place of residue 1A. Peptide E existed as a random coil (minimum at 204 nm) over a pH range of 4–9.8 at a peptide concentration of 0.20 mM (FIG. 6a), suggesting that 2A is not capable of forming the hydrogen-bonded hydrophobic cluster necessary for initiating β-sheet structure under conditions where peptide D adopts a β-sheet structure. A β-sheet structure is observed in peptide E at pH values >10. However, the lack of an isodichroic point suggests that the call to aggregated sheet structure is not well defined: i.e., intramolecular folding does not precede self-assembly. The concentration dependence of the CD spectra of peptide E suggested a self-associating β-sheet at concentrations above 0.20 mM at pH 10.6. Peptide F was prepared to probe the importance of hydrophobic cluster formation in β-sheet folding mediated by residue 1A. The flanking hydrophobic residues in peptide D were replaced with hydrophilic lysine residues in peptide F while maintaining a highly momologous amino acid composition and an amphiphilic periodicity of 2A. A 0.25 mM solution of peptide F was incapable of folding at pH 8.9, whereas 0.15 mM samples of peptide D adopted a β-sheet structure at this pH, implying that hydrophobic cluster interactions are critical for the function of 1A. Peptide F adopted a β-sheet structure above pH 9 (FIG. 6b), which may be explained by deprontonation of one of the two E-um-monium groups of the flanking Lys residues, allowing packing against one of the phenyl rings in 1A. More likely, intermolecular sheet formation is occurring as observed in (Val-Lys)$_n$ sequences. A self-association mechanism was supported by precipitation of insoluble aggregates above pH 9.8.

$^1$H NMR Studies of Peptides A and D–F. Classical NOESY and TOCSY experiments have been utilized to make sequence-specific resonance assignments for peptide A. The flanking residues of peptides D–F were similarly assigned. The remaining valine and lysine spin systems in peptides D–F were identified but not sequence specifically assigned due to resonance overlap.

Strong NOEs between the aromatic protons of residue 1 and the flanking Leu-3 δ- and δ'=methyl groups and the Val-5 γ- and γ'-methyl groups of peptide A were observed. NOEs were also evident between the aromatic protons of 1 and the γ-methylene proton of Leu-3 in this peptide. Peptide D exhibits analogous NOEs between the aromatic protons of residue 1 and the methyl groups of the flanking Val and Leu residues. Additional NOEs were seen between the aromatic protons and the Leu-6 β-, β'-, and γ-protons in peptide D. The observed NOEs support the existence of a hydrophobic cluster composed of the aromatic skeleton of residue 1A and the hydrophobic residues flanking 1A in both peptides A and D. Importantly, the NMR data were collected under conditions where these peptides are "unstructured" by far-UV CD. Hence, the hydrophobic cluster appears to be structurally organized and poised to nucleate β-sheet formation once solution conditions permit strand-strand interactions. This is consistent with other studies on peptides and proteins where hydrophobic clusters are observed to be stable under "denaturing" conditions and in the absence of a regular protein structure as discerned by far-UV CD. NOEs between the aromatic protons of residue 1A and the methylene groups of the flanking hydrophilic lysine side chains were not observed in peptide F. The inability of the lysine side chains to facilitate the formation of a hydrophobic cluster at pH values below the pK$_a$ of the ε-ammonium group (pH >8.9)

has also been observed in 4-(2-aminoethyl)-6-dibenzofuranpropionic acid-based heptapeptides, implying that alkyl side chains with an ammonium group at the terminus cannot pack efficiently against an aromatic ring. The methylene protons in the lysine side chains of peptide F exhibited no discernible upfield shift consistent with the lack of cluster formation at pH values >8.9.

The lack of observed NOEs between the aromatic protons of residue 2A and the methyl groups of the flanking valine and leucine residues in peptide E suggest that residue 2A cannot promote hydrophobic cluster formation consistent with the decreased flexibility of this residue. The methyl groups of the flanking Leu and Val residues in peptides A, D, and E exhibit upfield shifts of 0.1–0.2 ppm relative to those of the other valine residues in these sequences. The upfield shifts suggest that these peptides sample conformations where the methyl groups are in the diamagnetic shielding cones of the biphenyl ring systems of 1 and 2. However, the observation of an upfield shift alone is not an indication of hydrophobic cluster formation since 2 cannot promote hydrophobic cluster formation.

Information concerning the hydrogen-bonding network within a peptide containing residue 1A in aqueous solution was obtained from amide exchange studies of peptide A (3.0–3.3 mM, pH 3.4–3.6) and peptide D (2.5–2.9 mM, pH 4.1–5.1) where peptides A and D appear to be unstructured by far-UV CD. In both peptides, the rates of amide proton/deuterium exchange for the Leu and Val residues flanking 1 were at least an order of magnitude slower than the measurable rates for the remaining residues (Table 2). This suggests that the amide protons of the $\alpha$-amino acid residues flanking 1 are being protected from amide exchange by intramolecular hydrogen bonding. The residue specific amide NH assignments in combination with the amide exchange data strongly suggest that residue 1 promotes a 15-membered hydrogen-bonded ring conformation in aqueous solution; i.e., the $\alpha$-amino acid residues flanking 1 hydrogen bond with each other. In both peptides A and D, the amide proton of residue 1 exchanged too quickly to be observed within the time required to obtain the first NMR spectrum, suggesting that this amide proton is solvent exposed.

Determination of the Quaternary Structure of Peptide D. An associated, but soluble, $\beta$-sheet structure appears to form for peptides C and D as discerned from the pH and concentration dependent far-UV CD spectra. Insoluble aggregates were also observed for peptide C at higher concentrations (e.g., 0.25 mM) and/or pH values >7.5. Insoluble aggregates were observed for peptide D under highly alkaline conditions (pH >10, 0.15 mM). The implication behind these observations is that the intramolecular folding and self-associating equilibria are linked. The solution molecular weight of peptide D was evaluated by analytical equilibrium ultracentrifugation under conditions where $\beta$-sheet structure is observed by far-UV CD (e.g., 0.15 mmol, pH 9.1). The sedimentation of peptide D to the bottom of the ultracentrifugation cell was observed even at low rotor speeds, indicating that this peptide adopts a highly associated soluble $\beta$-sheet structure.

The soluble high molecular weight assemblies of peptide D were absorbed onto a carbon-coated copper grid from a 0.041 mM solution at pH 10.2 (10 mM borate buffer) and visualized with Ruthenium Red stain at a magnification of 80000x. The observed fibrils typically had dimensions of ~30 Å by 500–1000 Å. These dimensions are consistent with a cross-$\beta$-like structure in which the peptide has undergone intramolecular folding followed by self-assembly via intermolecular $\beta$-sheet formation. Fibril-fibril assemblies with widths of greater that 50 Å were also observed presumably as a result of protofilament assembly. It appears from these studies that peptide D undergoes intramolecular folding followed by self-association to afford a cross-$\beta$-sheet structure.

Characterization of Peptide G. The CD studies of peptide D suggest that the biphenyl-based amino acid 1 nucleates intramolecular antiparallel $\beta$-sheet folding, leading to a preorganized monomeric $\beta$-sheet structure which spontaneously self associates into a high molecular weight, cross-$\beta$-sheet structure. It seems reasonable that the incorporation of N-methylated amino acid residues into peptide D would unlink the folding and assembly equilibria, allowing a monomeric or dimeric $\beta$-sheet to be observed. Hence, peptide G (Table 1) was prepared to demonstrate that peptide D adopts a $\beta$-hairpin confirmation prior to self-assembly. The sequence of peptide G is identical to that of peptide D except that the Lys-3 and Lys-11 residues have been replaced with N-methylated Leu residues. The far-UV CD spectra of peptide G at 25° C. exhibit little dependence on pH, demonstrating that the replacement of two of the six Lys residues with noncharged residues affords a sheet structure which folds in a pH independent manner.[3n] The CD spectra exhibit minima at 198 and 223 nm, indicating that peptide G adopts both random coil and $\beta$-sheet structure. This observation is consistent with the peptide being structured in the region close to the $\beta$-turn and less structured at the termini of the strands due to fraying (vide infra). Also of interest is the shift of the $\beta$-sheet minimum to longer wavelengths relative to that of peptide D (223 nm versus 214 nm). Upon heating, peptide G exhibits an increase in $\beta$-sheet structure with a corresponding decrease in the random coil CD signal, but does not aggregate. This temperature sensitive increase in $\beta$-sheet structure is in accord with the anticipated importance of the hydrophobic effect toward the stability of the $\beta$-sheet structure in peptide G. The concentration dependent far-UV CD study of peptide G indicates that the peptide is monomeric as the means residue ellipticity (225 nm) remains constant over a concentration range of 0.015–0.4 mM (pH 7). Additionally, this peptide is monomeric within the concentration and pH ranges studied as shown by analytical equilibrium ultracentrifugation. The observed molecular weight of 1600±80 (0.11 mM, pH 6.8) compares well to the expected weight (1644) of the monomeric species.

The existence of extended structure within peptide G was also supported by FT-IR data. The amide I band which corresponds primarily to the C=O stretching vibration of the peptide bond is very sensitive to the peptide backbone conformation. An absorption between 1620 and 1640 cm$^{-1}$ is indicative of $\beta$-sheet structure. An additional weak band at 1670–1695 cm$^{-1}$ is specific to antiparallel $\beta$-sheet structure. Unordered peptides generally exhibit a carbonyl stretch at 1644 cm$^{-1}$ and may exhibit an absorption between 1657 and 1663 cm$^{-1}$. The FT-IR spectrum of a film of peptide G (formed from a 5.3 mM D$_2$O solution, pH 6.8) revealed a major band at 1631 cm$^{-1}$ consistent with $\beta$-sheet structure. Weak absorptions at 1657 and 1687 cm$^{-1}$ were also observed. The latter absorption is consistent with antiparallel structure, and the absorption at 1657 cm$^{-1}$ indicates random structure consistent with structural fraying at the termini. The FR-IR spectrum of the D$_2$O solution of peptide G exhibited absorptions at 1635 and 1684 cm$^{-1}$, again consistent with $\beta$-sheet structure. Absorptions at 1647, 1653, and 1662 cm$^{-1}$ which may arise from unstructured regions of the peptide were also observed. These data suggest a fluctuating $\beta$-sheet structure, consistent with the CD data.

Classical NOESY and TOCSY experiments were utilized to make sequence specific resonance assignments for peptide G. NOEs between the aromatic protons of residue 1 and the flanking Leu-6 α- and β-protons and the Val-8-γ- and γ'-methyl groups of peptide G were observed (FIG. 9). NOEs were also evident between the aromatic protons of 1 and the protons of the ethylene spacer between 1 and Val-8. As was seen in peptides A and D, the observed NOEs for peptide G support the existence of a hydrophobic cluster composed of the aromatic skeleton of residue 1 and the hydrophobic residues flanking 1. Strong interstrand NOEs of the type expected for a β-sheet in a protein are not observed in peptide G by 2D NOESY spectroscopy. Difference NOE methods which are currently in progress may reveal weak NOEs. Further evidence that peptide G is structured near the biphenyl template was provided by the observed $3J_\alpha NH$ coupling constants of $\geq 7.5$ Hz for the six residues nearest to 1. Coupling constants in the range of 7.5–10 Hz are expected for a β-sheet or an extended structure.

Amide exchange studies at pH 3.2 were used to examine the hydrogen-bonding properties of peptide G which is expected to be partially folded on the basis of the studies discussed above. The rates of amide proton exchange for Leu-6 and Val-8 (the residues flanking 1) as well as Val-4 and Val-10 (the next pair of intramolecular hydrogen-bonded residues in the β-sheet structure) were significantly slower than the measurable rates for the remaining residues (FIG. 9). As would be expected for a β-sheet conformation, the solvent-exposed lysine amide NHs exhibited the fastest amide exchange rates. The amide proton-deuterium exchange rates were studied in the random coil peptide H (having Gly-Gly in place of 1, Table 1) to demonstrate that the faster Lys amide exchange relative to the Val exchange was not simply a result of the nature of the side chain. The range of amide exchange rates was very narrow in peptide H compared to that of peptide G, suggesting that all of the amide protons in peptide H are in a nearly equivalent environment as would be expected for an unordered structure. Interestingly, both the slowest and fastest observed rates were for protons corresponding to valine residues in the unordered peptides while the lysine residues generally exhibited intermediate exchange rates. These data support the interpretation that the rate differences observed in peptide G are a result of differences in the amide proton environments rather than inherent differences between the valine and lysine amino acids.

The CD and FT-IR data in conjunction with the NMR Data support a well-defined structure in the vicinity of 1 with fraying of the β-sheet-like structure near the N- and C-termini. These results confirm that biphenyl-based residue 1 promotes intramolecular folding to afford a monomeric β-hairpin-like structure. In peptides which are capable of lateral association (such as peptide D), the monomeric β-sheet then undergo rapid self-association to form a β-sheet fibril.

Other Embodiments

From the above description, the essential characteristics of the present invention can be ascertained. Without departing from the spirit and scope thereof, various modifications can be made to adapt the compositions and methods of the invention to other usages.

Publications cited herein are incorporated by reference.

What is claimed is:

1. A β-sheet nucleating peptidomimetic, comprising
(a) a diarylheterocycle of the formula II:

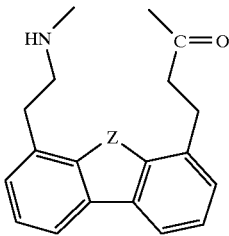
(II)

or the formula III:

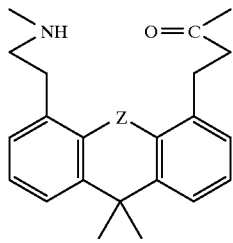
(III)

wherein Z is O, S, or $NR_a$, $R_a$ being $C_{1-6}$ alkyl;
  (b) a recognition strand of between 3 and 21 amino acid residues, said strand comprising
    a recognition sequence of a target protein which requires self-assembly for function,
    a first flanking amino acid residue $r^1$ selected from histidine and hydrophobic amino acids, wherein $r^1$ is between said recognition sequence and said diarylheterocycle, and is linked to said diarylheterocycle by an amide bond, and
    a first N-methylated residue adjacent to an intramolecularly hydrogen-bonded residue; and
  (c) a blocking strand of between 3 and 21 amino acid residues, said strand comprising
    a residue selected from valine, leucine, and isoleucine,
    a second flanking amino acid residue $b^1$ selected from histidine and hydrophobic amino acids, wherein said flanking residue is between said blocking strand and said diarylheterocycle, and is linked to said diarylheterocycle by an amide bond, and
    a second N-methylated residue adjacent to an intramolecularly hydrogen-bonded residue.

2. A mimetic of claim 1, wherein said blocking sequence further comprises amino acids such that the formal charge of said peptidomimetic is between 2.0 and 4.0 at physiological pH.

3. A mimetic of claim 1, wherein said blocking strand provides at least one residue $b^i$ which promotes interstrand interaction with a residue $r^i$ of said recognition strand.

4. A mimetic of claim 1, having at least two pairs of residues which promote interstrand interaction, each pair selected independently from the following pairs: ER, EK, FF, IY, FY, IF, II, IW, FW, IV, FV, FT, and IT.

5. A mimetic of claim 1, wherein each of said first and second N-methylated residues is a non-terminal residue.

6. A mimetic of claim 1, wherein at least one in every 8 residues is N-methylated.

7. A mimetic of claim 1, wherein said blocking strand has fewer residues than said recognition strand.

8. A mimetic of claim 1, wherein said mimetic is cyclic.

9. A mimetic of claim 1 having no more than 12 residues.

10. A mimetic of claim 9 having no more than 6 residues.

11. A mimetic of claim 10 having no more than 4 residues.

12. A mimetic of claim 1, wherein the diarylheterocycle has the formula II.

13. A mimetic of claim 1, wherein the diarylheterocycle has the formula III.

* * * * *